(12) United States Patent
Tofighi

(10) Patent No.: US 9,250,139 B2
(45) Date of Patent: Feb. 2, 2016

(54) SYSTEM AND METHOD FOR COMBINED MICROWAVE HEATING AND RADIOMETRY FOR CHARACTERIZING BIOLOGICAL TISSUES

(71) Applicant: Mohammad-Reza Tofighi, Malvern, PA (US)

(72) Inventor: Mohammad-Reza Tofighi, Malvern, PA (US)

(73) Assignee: THE PENN STATE RESEARCH FOUNDATION, University Park, PA (US)

(*) Notice: Subject to any disclaimer, the term of this patent is extended or adjusted under 35 U.S.C. 154(b) by 290 days.

(21) Appl. No.: 13/788,231

(22) Filed: Mar. 7, 2013

(65) Prior Publication Data
US 2013/0272339 A1    Oct. 17, 2013

Related U.S. Application Data

(60) Provisional application No. 61/625,133, filed on Apr. 17, 2012.

(51) Int. Cl.
*A61B 5/00* (2006.01)
*G01K 11/00* (2006.01)
(Continued)

(52) U.S. Cl.
CPC ............. *G01K 11/006* (2013.01); *A61B 5/026* (2013.01); *A61B 5/027* (2013.01); *A61B 5/0265* (2013.01); *A61B 18/1815* (2013.01); *A61B 2018/183* (2013.01); *A61B 2018/1823* (2013.01)

(58) Field of Classification Search
CPC ...... A61B 5/026; A61B 5/0265; A61B 5/027; A61B 18/1815; A61B 18/1823; A61B 18/183; A61B 18/1838; A61B 18/1846; A61B 18/1853
USPC .......... 600/549, 430, 474, 427; 374/120–122, 374/E11.003
See application file for complete search history.

(56) References Cited

U.S. PATENT DOCUMENTS 4,416,552 A * 11/1983 Hessemer et al. ............. 374/117
4,815,479 A *  3/1989 Carr .............................. 607/102
(Continued)

FOREIGN PATENT DOCUMENTS

EP         0648515         4/1995

OTHER PUBLICATIONS

Brooker, Graham. Sensors and Signal. Chapter 4. Millimeter Wave Radiometers. 2007. <http://www.acfr.usyd.edu.au/pdfs/training/sensorSystems/04%020Millimetre%20Wave%20Radiometers.pdf>.*

(Continued)

*Primary Examiner* — Max Noori
*Assistant Examiner* — Jonathan Dunlap
(74) *Attorney, Agent, or Firm* — Novak Druce Connolly Bove + Quigg LLP

(57) ABSTRACT

Systems and methods are provided for characterizing biological tissues through their thermal signatures that include directing microwave energy into a biological tissue using a first slot antenna, detecting microwave radiation emitted by the biological tissue using a second slot antenna, generating output signals corresponding to the microwave radiation, processing the output signals to characterize a temperature of the biological tissue as a function of time to yield temperature characteristics, and characterizing a biological function of the biological tissue based on the temperature characteristics. The first and second slot antennas can be defined using a dual mode antenna and the generating can include alternatively collecting signals from the second slot antenna through a first low noise amplifier (LNA) and a reference load through a second LNA that the two LNAs are substantially identical.

13 Claims, 14 Drawing Sheets

(51) Int. Cl.
*A61B 5/026* (2006.01)
*A61B 5/0265* (2006.01)
*A61B 18/18* (2006.01)
*A61B 5/027* (2006.01)

(56) References Cited

U.S. PATENT DOCUMENTS

| | | | | |
|---|---|---|---|---|
| 5,531,662 | A * | 7/1996 | Carr | 600/2 |
| 6,424,869 | B1 * | 7/2002 | Carr et al. | 607/101 |
| 6,543,933 | B2 * | 4/2003 | Stergiopoulos et al. | 374/122 |
| 8,062,228 | B2 * | 11/2011 | Carr | 600/549 |
| 8,574,166 | B2 * | 11/2013 | Carr | 600/549 |
| 8,915,904 | B2 * | 12/2014 | Brennan et al. | 604/891.1 |
| 8,926,605 | B2 * | 1/2015 | McCarthy et al. | 606/34 |
| 8,932,284 | B2 * | 1/2015 | McCarthy et al. | 606/34 |
| 8,934,953 | B2 * | 1/2015 | Carr et al. | 600/329 |
| 8,954,161 | B2 * | 2/2015 | McCarthy et al. | 607/102 |
| 8,981,794 | B2 * | 3/2015 | Gritz et al. | 324/647 |
| 2002/0126731 | A1 * | 9/2002 | Stergiopoulos et al. | 374/122 |
| 2005/0063447 | A1 * | 3/2005 | Ammar | 374/1 |
| 2006/0265034 | A1 * | 11/2006 | Aknine et al. | 607/101 |
| 2009/0012417 | A1 * | 1/2009 | Carr | 600/549 |
| 2009/0221932 | A1 | 9/2009 | Butz et al. | |
| 2012/0029381 | A1 * | 2/2012 | Carr | 600/549 |
| 2012/0283534 | A1 * | 11/2012 | Carr et al. | 600/324 |
| 2013/0204240 | A1 * | 8/2013 | McCarthy et al. | 606/21 |
| 2013/0324993 | A1 * | 12/2013 | McCarthy et al. | 606/33 |
| 2014/0065664 | A1 * | 3/2014 | Aknine et al. | 435/29 |
| 2014/0303614 | A1 * | 10/2014 | McCarthy et al. | 606/34 |
| 2014/0343374 | A1 * | 11/2014 | Carr et al. | 600/301 |

OTHER PUBLICATIONS

"Circular". The American Heritage Dictionary of the English Language, Fifth Edition. Houghton Mifflin Harcourt Publishing Company. Accessed online Jul. 27, 2015. <https://www.ahdictionary.com/word/search.html?q=circular>.*

Anderson et al., "Self-heated thermistor measurements of perfusion," IEEE Trans. Biomed. Eng. (Sep. 1992) 39(9): 877-885.

Bardati et al., "Microwave radiometry for medical thermal imaging: Theory and experiment," IEEE International Microwave Symposium (Jun. 1992): 1287-1290.

Carlier et al., "Modeling of planar applicators for microwave thermotherapy," IEEE Trans. Microwave Theory Tech. (Dec. 2002) 50(12): 3036-3042.

Devine and Tofighi, "Class E Colpitts Oscillator for low power wireless applications," Electronics Letters, (Oct. 2008) 44(21): 1257-1258.

Gabriel et al., "The dielectric properties of biological tissues: III. Parametric models for the dielectric spectrum of tissues," Phys. Med. Biol (Nov. 1996) 41(11): 2271-2293.

Gibbs, "A thermoelectric blood flow recorder in the form of a needle," Proc. Soc. Exptl. Biol. Med. (1933) 31: 141-147.

Jacobsen and Klemetsen, "Improved detectability in medical microwave radio-thermometers as obtained by active antennas," IEEE Transactions on Biomedical Engineering (Dec. 2008) 55(12): 2778-2785.

Jacobsen et al., "Dual-mode antenna design for microwave heating and noninvasive thermometry of superficial tissue disease," IEEE Trans. Biomed. Eng. (Nov. 2000) 47: 1500-1509.

Karacolak et al., "Design of a dual-band implantable antenna and development of skin mimicking gels for continuous glucose monitoring," *IEEE Trans. Microwave Theory Tech* (Apr. 2008) 56(4): 1001-1008.

Kawoos et al., "In-vitro and in-vivo trans-scalp evaluation of an intracranial pressure implant at 2.4 GHz," IEEE Trans. Microwave Theory Tech. (Oct. 2008) 56(10): 2356-2365.

Kummer and Gillespie, "Antenna measurements—1978," Proceedings of the IEEE (Apr. 1978) 66(4): 483-507.

Liu and Xu, "Estimation of blood perfusion using phase shift in temperature response to sinusoidal heating at the skin surface," IEEE Trans. Biomed. Eng. (Sep. 1999) 46(9): 1037-1043.

Maruyma et al., "Feasibility of noninvasive measurement of deep brain temperature in newborn infants by multifrequency microwave radiometry," IEEE Trans. Microwave Theory Tech. (Nov. 2000) 48(11): 2141-2147.

Meng et al., "Digital microwave system for monitoring intracranial pressure in hydrocephalic and traumatic brain injury patients," Digest of 2011 International Microwave Symposium (Jun. 2011) Baltimore, MD.(4 pages).

Mudalier et al., "A phantom tissue system for the calibration of perfusion measurements," J Biomech Eng. (Oct. 2008) 130(5): 051002.

O'Reilly et al., "Development of a noninvasive blood perfusion probe," Advances in Heat and Mass Transfer in Biotechnology, (1996): HTD-337/BED-34: 67-73, ASME.

Ojica et al., "Microwaves and infrared thermography—Comparative studies in early breast cancer detection," *7th* International Symposium on Advanced Topics in Electrical Engineering (ATEE) (May 2011): 1-4.

Patel et al., "A self-heated thermistor technique to measure blood flow from the tissue surface," ASME Winter Annual Meeting (Dec. 1986): 1-6, Anaheim, CA.

Scott et al., "Development of methodologies for the estimation of blood perfusion using a minimally invasive thermal probe," Meas. Sci. Technol. (1998) 9: 888-897.

Selvan, "Preliminary examination of a modified three-antenna gain measurement method to simplify uncertainty estimation," IEEE Antennas Propagat. Mag. (Apr. 2003) 45(2): 78-81.

Staebell and Misra, "An experimental technique for in vivo permittivity measurement of materials at microwave frequencies," IEEE Trans. Microwave Theory and Tech. (Mar. 1990) 38(3): 337-339.

Stauffer et al., "Radiation patterns of dual concentric conductor microstrip antennas for superficial hyperthermia," IEEE Trans. Biomed. Eng. (May 1998) 45(5): 605-613.

Sterzer, "Microwave radiometers for non-invasive measurements of subsurface tissue temperatures," Automedica, (Sep. 1987) 8: 203-211.

Thomy et al., "New antenna-sensor for temperature control by microwave radiometry," *Proceedings of IEEE International Conference on Sensors* Nov. (2002) 2: 1308-1312.

Tofighi and Sunal, "Spiral antenna irradiation into Lossy Media with Debye dispersion," Proceedings of IEEE Radio and Wireless Symposium (Jan. 2008): 311-314, Orlando, FL.

Tofighi, "FDTD modeling of biological tissues Cole-Cole dispersion for 0.5 to 30 GHz using relaxation time distribution samples—novel and improved implementations," IEEE Trans. Microwave Theory Tech. (Oct. 2009) 57(10): 2588-2596.

Ulaby et al., "Radiometer systems" Chapter 6 in Microwave Remote Sensing Fundamentals and Radiometry, Addison-Wesley Publishing Company: Massachusetts, 1981: 344-431.

Vander Vorst et al., "RF/microwave interaction with biological tissues," Wiley: Hoboken, NJ, 2006. (342 pages).

Warty et al., "Characterization of implantable antennas for intracranial pressure monitoring: Reflection by and transmission through a scalp phantom," IEEE Trans. Microwave Theory Tech. (Oct. 2008) 56(10): 2366-2376.

International Search Report and the Written Opinion of the ISA mailed on Jun. 14, 2013 in PCT Application PCT/US2013/029527, international filing date Mar. 7, 2013. (6 pages).

* cited by examiner

SYSTEM AND METHOD FOR COMBINED MICROWAVE HEATING AND RADIOMETRY FOR CHARACTERIZING BIOLOGICAL TISSUES

CROSS-REFERENCE TO RELATED APPLICATIONS

This application claims priority to U.S. Provisional Patent Application No. 61/625,133, entitled SYSTEM AND METHOD FOR COMBINED MICROWAVE HEATING AND RADIOMETRY FOR CHARACTERIZING BIOLOGICAL TISSUES and filed Apr. 17, 2012, the contents of which are herein incorporated by reference in their entirety.

FIELD OF THE INVENTION

The present invention relates to, and more specifically to apparatus and methods for characterizing biological tissues based on microwave heating and radiometry.

BACKGROUND

Blood perfusion is an important component of the physiology of normal tissue, local transport of oxygen, nutrients, and pharmaceuticals. Among clinical applications that the knowledge perfusion is necessary are disease diagnostics, drug delivery, cancer hyperthermia treatment, skin perfusion after plastic surgery (involving the use of flaps, i.e., sections of living skin and underlying muscle that are surgically moved from one area of the body to another), and the management of peripheral vascular disease (a major cause of amputations).

SUMMARY

Embodiments of the invention concern systems and methods for characterizing biological tissues based on microwave heating and radiometry.

In a first embodiment of the invention, a system is provided. The system includes a dual mode antenna defining a first slot antenna and a second slot antenna. The system also includes a microwave radiometer coupled to the first slot antenna and a microwave source coupled to the second slot antenna. The system further includes a controller coupled to the microwave radiometer and the microwave source. In the system, the controller operates the dual mode antenna in a heating mode via operation of the microwave source and in a temperature measurement mode via operation of the microwave radiometer.

The dual mode antenna can consist of a metallization layer that includes a first slot for defining the first slot antenna and a second slot for defining the second slot antenna. The dual mode antenna can further include substrate layer supporting the metallization layer, a superstrate layer disposed on the metallization layer, a first feed coupled to the first slot antenna, and a second feed coupled to the second slot antenna. Additionally, the first slot can extend along a circular path and the second slot can extend along a rectangular path. Also, the first slot can be nested with respect to the second slot. The two feeds are in right angle (i.e., 90 degrees) with respect to the center of the structure. This is important in preventing significant leakage of the strong microwave heating signal to the radiometer input.

In the system, the radiometer can include a front module coupled to the first slot antenna and a rear module coupling the front module to the controller. The front module can include a two-way switch with an output port, a first input port, and a second input port. The front module can also include a first low noise amplifier (LNA) coupled between the first input port and the first slot antenna and a second LNA coupled between the second input port and a reference load. In this configuration, the first LNA and the second LNA are substantially identical. Further, the two-way switch can be controlled by the controller to selectively couple the output port to one of the first input port and the second input port.

The radiometer further can also include an intermediate frequency (IF) module coupling the front module to the rear module. The IF module can include a synthesizer and a mixer, where the mixer receives an output of the front module, mixes the output of the front module with an output of the synthesizer to yield a (frequency) down-converted output, and forwards the down-converted output to the rear module.

The rear module can include a band pass filter (or a low pass filter if the IF module is used) having an input coupled to the front module and a detector having an input coupled to the output of the filter and an output coupled to the controller.

In a second embodiment of the invention, a method is provided. The method includes the steps of directing microwave energy into a biological tissue using a first slot antenna during a first time period and detecting microwave radiation emitted by the biological tissue using a second slot antenna during a second time period subsequent to the first time period. The method also includes the steps of generating output signals corresponding to the microwave thermal (black body) radiation and processing the output signals to characterize a temperature of the biological tissue as a function of time to yield temperature characteristics.

The method additionally includes the step of characterizing a biological function of the biological tissue based on the temperature characteristics. In one configuration, the biological function is a blood perfusion rate.

In the method, the steps of directing and detecting can be performed using a dual mode antenna defining the first slot antenna and the second slot antenna. Accordingly, the directing includes coupling the first slot antenna of the dual mode antenna to a microwave source during the first time period and the detecting includes coupling a microwave radiometer to the second slot antenna of the dual mode antenna during the second time period.

The dual mode antenna can be selected to include metallization layer having a first slot for defining the first slot antenna and a second slot for defining the second slot antenna. The first slot can be extended along a rectangular path and the second slot can be extended along a circular path. Further, the second slot to be nested with respect to the first slot.

In the method, the generation of the temperature related voltage (i.e., the radiometer output signal) can include collecting signal from the second slot antenna through a first low noise amplifier (LNA) and a reference load through a second LNA to yield the output signal, where the first and second LNAs are substantially identical. Further, the generation can include mixing the signal at the output of front module with signal from a synthesizer to yield a frequency down-converted signal before the detector that generates the output signal of the rear module.

DETAILED DESCRIPTION

Figure 1:
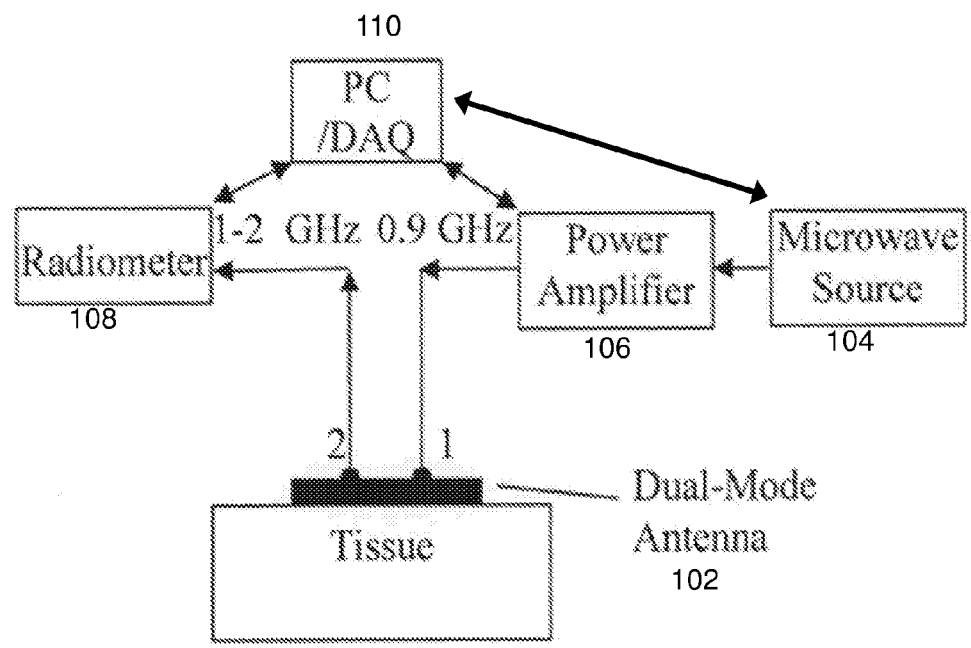
FIG. 1 shows a block diagram for a exemplary system in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments of the invention provide a new approach to characterizing biological tissues. In particular, the various embodiments of the invention provide methods of characterizing biological tissues, and devices therefrom, that operate by heating the biological tissues of a subject using microwave heating and monitoring the temperature decay using microwave radiometric sensing. As used herein, the term "biological tissue" refers to any tissues of an organism, including plants, animals, or humans. The rate of temperature decay correlates with characteristics of biological tissues. For example, the rate of temperature decay correlates with the blood perfusion rate, thus allowing the actual blood perfusion rate of the subject to be determined. Such techniques can be applied completely noninvasive and tetherless. Further, such techniques allow a measurement of characteristics within the biological tissues of the subject, rather than just the perfusion rate associated with the surface of skin. In addition, the techniques can be equally used in characterizing non-biological subjects, with microwave properties similar to those of the biological tissues. For example, the techniques can be used in measurement of flow rate of water or other liquids flowing within a non-metallic tubing.

As noted above, one type of characterization possible by the systems and methods described herein is characterization of blood perfusion rate. Although the various embodiments will be described generally with respect to blood perfusion rate, the systems and methods described here can be applied to other types of characterization of biological tissues that correspond with temperature decay characteristics. The remainder of the discussion will be directed at blood perfusion measurements, but only for ease of illustration and not by way of limitation. Also, the same type of characterization can be equally done from the temperature rise characteristics as well. Non-simultaneous microwave heating and microwave monitoring periods is preferred to reduce microwave interference during the monitoring period.

Some basic concepts for utilizing microwave heating for blood perfusion measurement have been described elsewhere, where a heating microwave source was suggested for use in order to raise the temperature of the tissue. The present invention builds on this previous work via the combination of such microwave heating and microwave radiometry. That is, the present invention provides a dual-mode microwave system (i.e., combining microwave heating and microwave radiometry) to provide a novel solution for completely noninvasive blood perfusion measurement.

One aspect of the various embodiments is the utilization of a novel dual-mode antenna system, with two separate input ports for heating and radiometry. Another aspect of the various embodiments other is the introduction of two identical low noise amplifiers (LNA) before a so-called "Dicke switch" that repeatedly switches between the radiometry antenna and a reference temperature load of the system. These two aspects, along with the concept of the combined microwave heating and radiometry for blood perfusion evaluation, thus provide novel systems and methods for the measurement of blood perfusion and other biological characteristics.

Previous techniques suggested for blood perfusion measurement have been primarily based on direct heating of the tissue surface by a heat source and recording the temperature change by a temperature sensor in contact with the subject, such as a thermistor, invasively or noninvasively. Ignoring the drawbacks of invasive methods (e.g., patient discomfort, tissue trauma, and local infections) such conventional techniques suffer from the large error in the estimation of the perfusion due to an imperfect contact of the temperature sensor to the subject.

In view of the foregoing, there is a need for a reliable tissue perfusion measurement system with the following specifications:

1. simple to use—physician just applies it to skin or tissue;
2. rapid—results in less than one minute;
3. repeatable—can be used many times in one session—no cumulative issues with exposure in normal use;
4. painless—no injection or puncture required;
5. reliable—not dependent on skin translucency for function;
6. portable—physician can take device to bedside for inpatient;
7. inexpensive—unlimited lifetime for basic device so cost is amortized over hundreds or thousands of tests.

Therefore in view of the limitations of conventional methods and the necessity for improvement, the various embodiments of the invention provide a new dual-mode microwave unit that satisfies all or most of the above requirements. In particular, the various embodiments provide systems and methods for utilizing microwave irradiation for heating the tissue and microwave radiometry for tissue temperature measurement.

An exemplary block diagram for a system in accordance with the various embodiments is illustrated in FIG. 1. As shown in FIG. 1, the system 100 includes a dual mode antenna 102 that is placed in contact with the tissues of the subject. The dual mode antenna 102 is coupled to a microwave source 104 through a power amplifier 106. The dual mode antenna 102 is also coupled to a radiometer 108. The microwave source 104, radiometer 108 and the power amplifier 106 can be coupled to a controller 110, such as a computer or other data acquisition system, to control the overall operation of the system.

In operation, the controller 110 controls the microwave source 104 and the power amplifier 106 to deliver, via the dual mode antenna 102, microwave radiation for raising tissue temperature by a small amount, such as 1° C. or less. The controller 110 then discontinues delivery of the microwave radiation and utilizes the radiometer 108 to measure the rate of decay of temperature. The measured decay of the temperature is then used to obtain the blood perfusion rate. As used herein, the term "blood perfusion rate" refers to the blood volume flow rate in microcirculation (capillary network, arterioles, venules) through a given volume of tissue.

Figure 2:
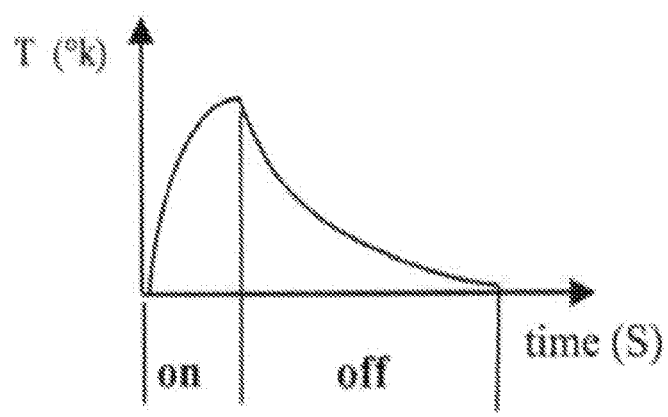
FIG. 2 shows an x-y plot of temperature of biological tissues as a function of time during and after heating of the biological tissues.

An exemplary plot of temperature of tissue as a function of time is illustrated in FIG. 2. As shown in FIG. 2, while the microwave radiation is being delivered ("on"), the temperature of the tissue can be quickly elevated to a desired temperature. For example, temperature can be raised by 1° C. or less, as described above. However, the various embodiments are not limited in this regard and temperature can be raised by other amounts. Once the delivery of microwave radiation is terminated ("off"), the temperature drops in accordance with a function that correlates to the blood perfusion rate.

Radiometer Configuration

In the various embodiments, the radiometer measurements are performed using a modified "Dicke" radiometer configuration. In a conventional Dicke radiometer, temperature is measured via collection of signals from a source of interest and a reference. These signals are collected by providing a switch for alternating collection between the output of a radiometer antenna and the output of a reference load that is kept at a constant temperature. The difference between the signals can then be used to determine temperature.

In conventional microwave radiometric systems based on a Dicke radiometer, since the radiometer essentially measures the thermal radiation (i.e. noise) emitted by the target tissue, the radiometric signal (brightness temperature) to be measured can be obscured by (1) noise generated inside the system and (2) the gain fluctuation in the system.

To overcome the latter limitation, conventional Dicke radiometers are typically configured to utilize a switching at a constant rate of the input to the radiometer system between the antenna and the reference load. As a result, the adverse effects of any system fluctuations that both signals equally detect can be reduced or eliminated, as the final output after the detection would be proportional to the temperature difference between the antenna and the reference temperature load.

To overcome the former limitation, the various embodiments include a modified configuration of the conventional Dicke radiometer. In particular, this modified configuration includes two low noise amplifiers (LNAs) for both antenna and reference temperature input paths. These LNAs are selected to be identical or substantially identical. That is, any variation in the characteristics of such LNAs should be 20% or less, such as 10%, 5%, or less. In some embodiments, the LNAs can be internal and can be integrated as part of the front-end electronics. This configuration leads to an increase in the sensitivity of the radiometer and provides a significant advancement over other conventional systems. It has been observed that radiometer detectability, quantified by increased probability to correctly detect a deep-seated hot object, is improved significantly by introducing that external LNA. On the other hand, it is known that the minimum temperature resolution of a Dicke radiometer is $$\Delta T = \frac{2(T_A + T_{Rec})}{\sqrt{B\tau}} \qquad (1)$$

and is achieved when $T_A = T_{Ref}$, where $T_A$, $T_{Ref}$ and $T_{Rec}$ are the antenna temperature, reference temperature, and the receiver noise temperature. Also, B and t are the radiometer bandwidth and integration time respectively. By integration of the two identical LNAs in both reference temperature and antenna paths, the temperature resolution is expected to be kept close to its minimum, while the sensitivity is being increased. Therefore, the lowest temperature resolution is expected to be achieved when $T_{Ref}$ is set to around the body's temperature of 37° C.

A block diagram of an exemplary configuration of a radiometer 300 in accordance with the various embodiments and the principles described above is illustrated with respect to FIG. 3A. Such a design can be used to implement and utilize the radiometer 108 in FIG. 1. However, the exemplary configuration of FIG. 3A is but one possible architecture for a radiometer in accordance with an exemplary embodiment.

Figure 3A:
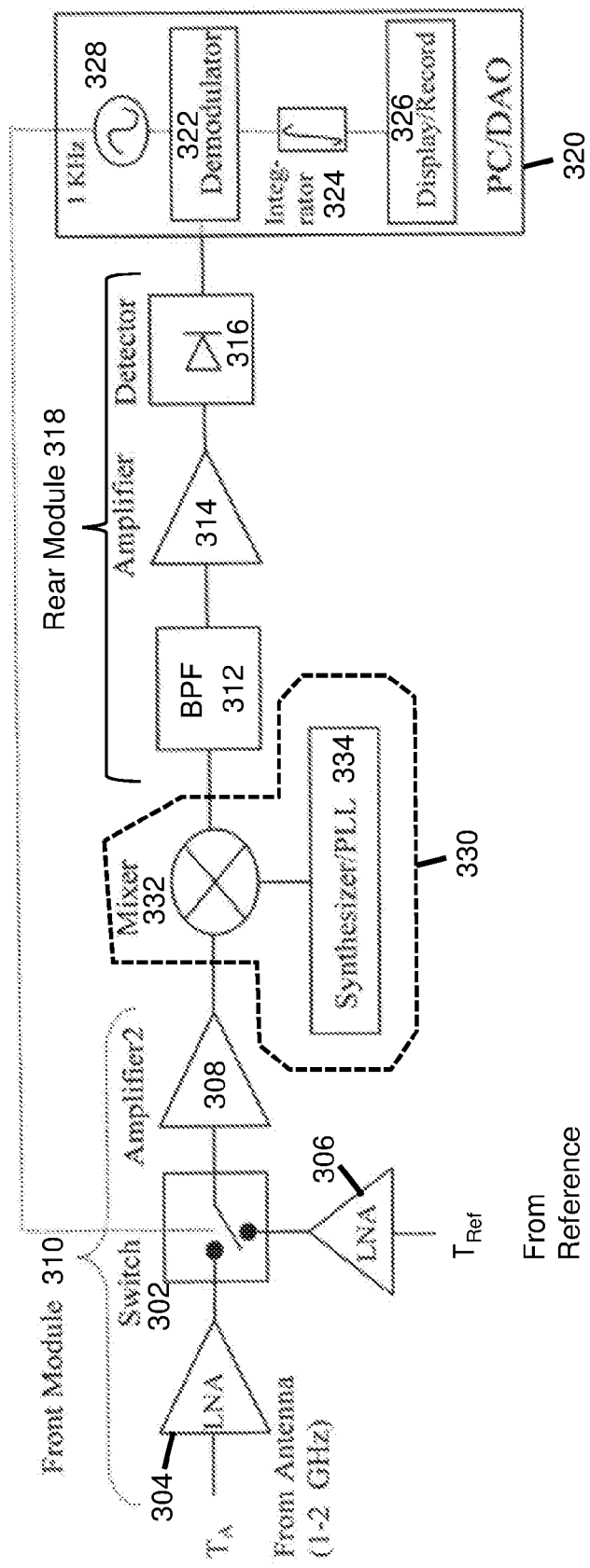
FIG. 3A shows block diagram for an exemplary configuration of a radiometer in accordance with the various embodiments.
Figure 3B:
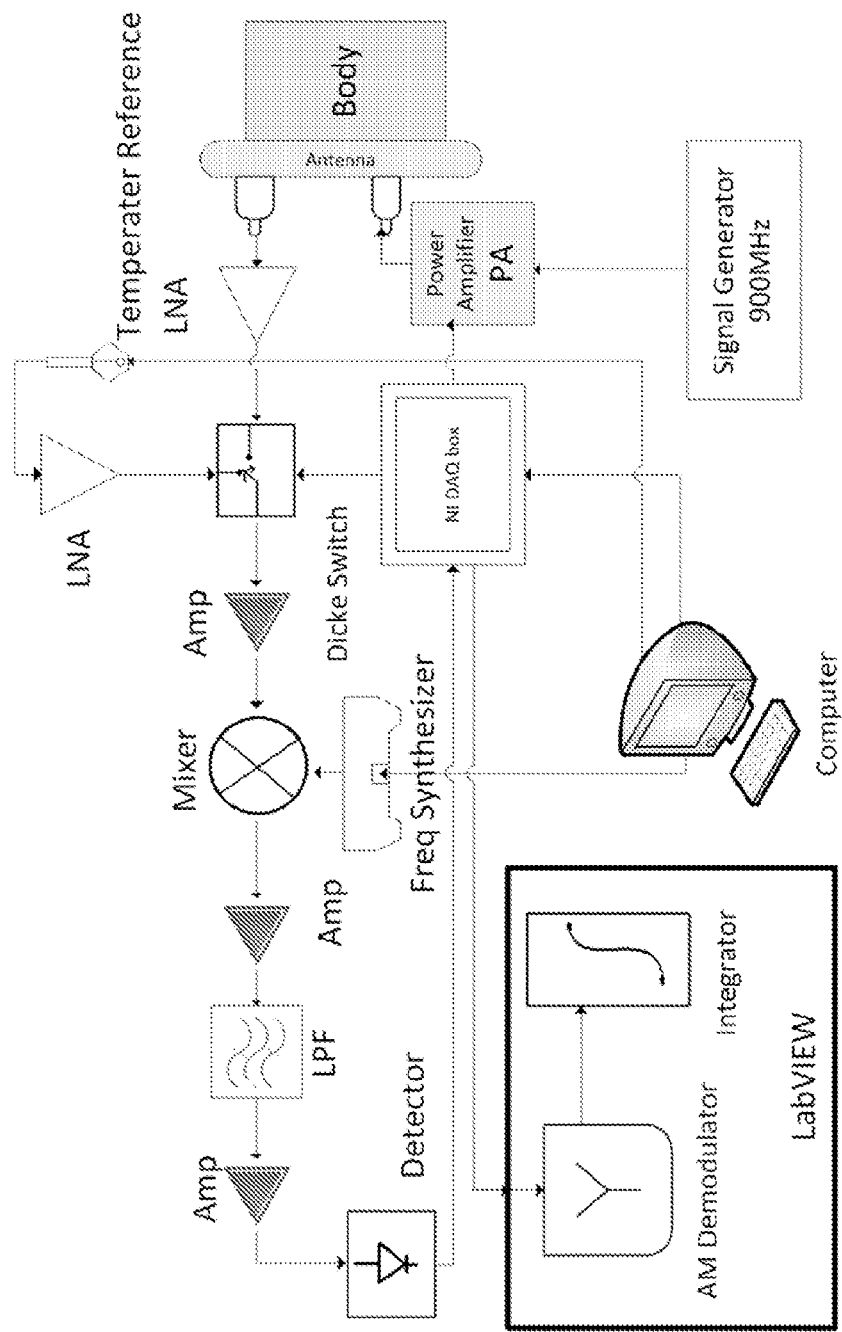
FIG. 3B shows block diagram for another exemplary configuration of a radiometer in accordance with the various embodiments.

For example, FIG. 3B illustrates an alternative configuration 350 having a similar arrangement of components than the components in FIG. 3A. Further, in the various embodiments, a radiometer can include more or less components than illustrated in FIG. 3A or 3B.

As shown in FIG. 3A, the radiometer 300 can include a switch 302 for switching between signals from an antenna, $T_A$, and signals from the reference load, $T_{ref}$. As noted above, the signals $T_A$ and $T_{Ref}$ are passed through corresponding ones of identical LNAs 304 and 306 before reaching switch 302. As shown in FIG. 3A, the output of switch 302 can be passed through a first amplifier 308. Together, the switch 302, the LNAs 304 and 306, and the amplifier 308 can define a front module 310 of the radiometer 300.

In a single channel configuration of radiometer 300, the output of front module 310 can be provided to a band pass filter 312 to fix the radiometry range for the radiometer 300. The output of the band pass filter 312 can be amplified, via amplifier 314. This amplified output of the band pass filter 312 can be then detected via a detector 316. A "band pass filter", as used herein, refers to any type of filter that filters out any range of frequencies from a signal. Thus, a band pass filter can encompass not only filters for specific ranges of frequencies, but also conventional low-pass and high-pass filters. Together, the band pass filter 312, the amplifier 314, and the detector 316 can define a rear module 318 of the radiometer.

The output signals of the rear module 318 can then be provided to a controller 320, such as a computer or data acquisition system to process the output signals and generate temperature information. The controller 320 can include a demodulator 322 and an integrator 324 for generating temperature information for a display or record 326. There are also alternative embodiments of the controller 320 possible. For example, the demodulator 322 can be moved from the controller 320 to the rear module 318. The controller 320 can also include a signal generator 328 for concerting operation of the demodulator 328 and the switch 302 in the front module 310.

In operation, the detector converts the filtered and amplified microwave signal to a low frequency voltage having a modulation component corresponding to the signal generator's frequency. This modulation is removed by the demodulator followed by the integrator, yielding an output DC voltage proportional to the temperature. To obtain the temperature from this voltage however requires performing a calibration. The calibration procedure is performed using a setup where the temperature of a tissue mimicking liquid in a container is controlled using a temperature regulation mechanism, is simultaneously measured by the radiometer, and is compared against the output voltage provided by the radiometer. Thereby, a "calibration curve" of voltage versus temperature is obtained and is used in subsequent radiometer measurements of biological tissues' temperature.

Although radiometer 300 with the mentioned calibration curve can provide an "absolute temperature", such an absolute temperature measurement may not be necessary in certain situations. For instance, it is likely that for the small temperature changes of 1° C. or less, the voltage changes with the temperature linearly, and the "relative voltage change" could be accurately related to a "relative temperature change" (say within 1%, 5%, and so on). In that case, from such a relative measurement, the perfusion information could be estimated without the need for exact determination of the baseline body temperature (usually about 37 C.). Although radiometer 300 has been describe above for use in a single channel mode, the radiometer 300 can also be configured with an intermediate frequency (IF) stage 330 to provide a multi-channel configuration. In particular, the IF stage 330 can be placed between the front module 310 and the rear module 318 to allow the operating frequency range to be varied. In particular, the IF stage 330 can be implemented as a mixer 332 for receiving signals from the front module 310 and mixing this with a signal from a frequency synthesizer 334 to select a portion of the microwave band to operate in. For example, the frequency synthesizer 334 can be programmed for 0.9, 1.2, 1.5, 1.8, and 2.1 GHz, i.e. a five channel operation. If the filter BPF 312 is designed to pass radiometric signals from 0 to 0.15 GHz, each channel would then cover a range of 300 MHz bandwidth (e.g., Channel 3: 1.35 to 1.65 GHz). Because the penetration depth of microwave signal decreases with increasing the channels' frequency, a depth related temperature characteristics can be obtained by such a multichannel operation.

Antenna Configuration

As noted above, in addition to the novel radiometer configuration, the various embodiments also implement a novel dual-mode antenna. This antenna consists of a rectangular annular slot for heating at microwave frequencies (e.g., at 900 MHz) and a circular annular slot for radiometric sensing at microwave frequencies (e.g., at 1-2 GHz), where the circular annular slot is surrounded by or nested with respect to the rectangular annular slot. As used herein, the term "annular slot" refers to a slot or channel that forms continuous, closed loop. This particular nested configuration was derived by the inventor by conducting the analysis through simulation of individual rectangular and circular annular slots, where the former is intended for heating at 915 MH and the latter for radiometry about 1.5 GHz.

Rectangular and circular annular slot antennas have been shown to exhibit desirable specific absorption rate (SAR, i.e., power deposition) pattern in the tissue. The suggested feed network for the annular slot may consist of a microstrip feed structure, feeding a patch laid out on the backplane and fed at multiple points, or relatively long microstrip lines on the backplane to feed the slot. For the blood perfusion evaluation, these antennas can be configured as a dual-mode structure to offer an attractive solution for combined heating and radiometric sensing.

The main advantage of using such a two-input dual-mode antenna is avoiding high power/low insertion loss duplexers when a single-input antenna is used. A simple feeding strategy is incorporated to keep the coupling between the two feeds ($S_{21}$) low, where the two feed points are spatially apart for 90° with respect to one another. They are directly fed by coaxial lines instead of the microstrip lines. Lowering cable attenuation by using a short coaxial cable length is also advantageous, when minimal degradation of the antenna noise temperature by the feeding transmission line is desirable for the radiometric sensing. Two small rectangular metallization areas are added on the back of the substrate to accommodate the attachment of coaxial launchers.

Figure 4A:
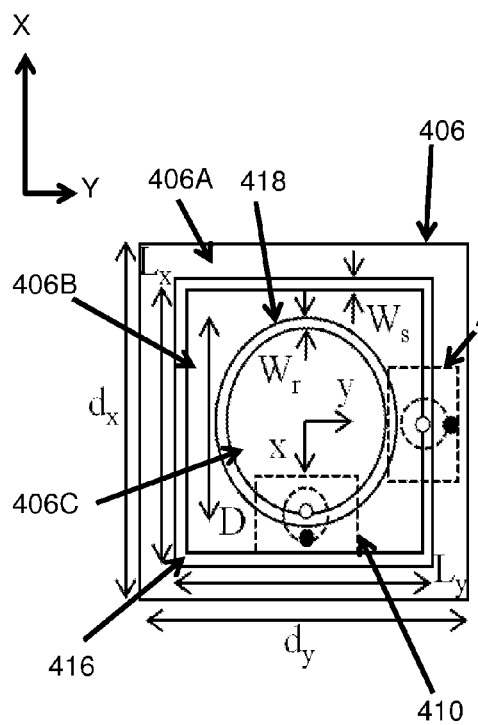
FIG. 4A is a top view of an exemplary dual mode antenna in accordance with the various embodiments.
Figure 4B:
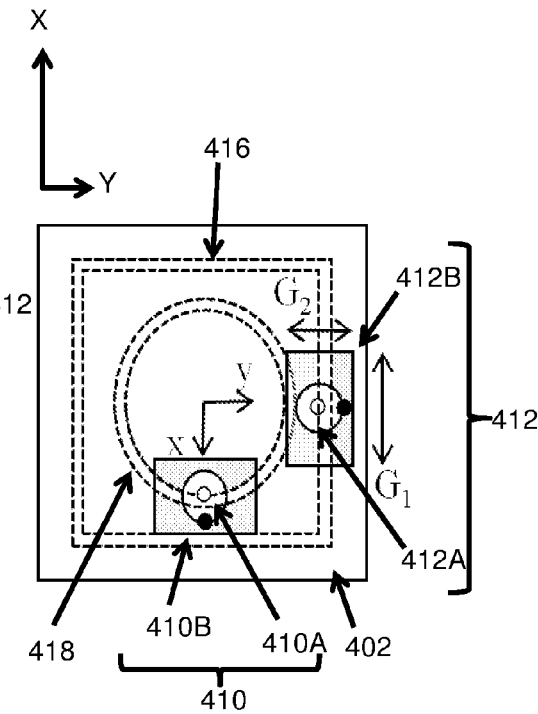
FIGS. 4B and 4C are bottom view and side partial cross-section view of the dual mode antenna of FIG. 4A respectively.
Figure 4C:
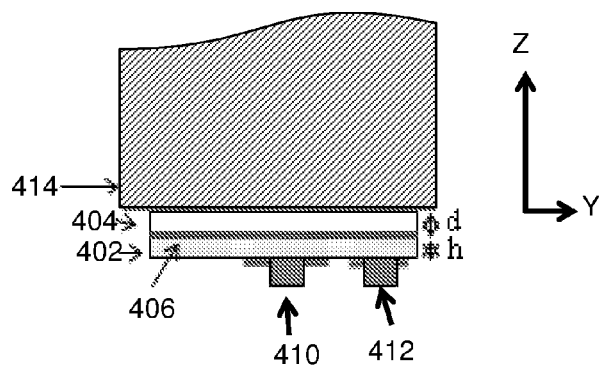

One such configuration is illustrated below with respect to FIGS. 4A, 4B, and 4C. FIGS. 4A, 4B, and 4C are top, bottom, and side views, respectively, of an exemplary dual mode antenna 400 in accordance with the various embodiments. As shown in FIG. 4C, the dual mode antenna 400 can be implemented as a series of layers. In particular, the layers include a substrate layer 402 with a height h, a superstrate layer 404 with a thickness d, and a metallization/slot (MS) layer 406 formed in between layers 402 and 404. Additionally, the dual mode antenna 400 includes first and second feeds 410 and 412 for connecting to the slot antennas formed in MS layer 406. The feeds 410 and 412 connect and extend through the substrate layer 404 to allow connection to the rest of the system.

In operation, the exposed surface of superstrate layer 404 can be placed in proximity to or in contact with the tissue 414 of the subject to provide microwave heating and microwave radiometric sensing via the slot antennas formed in MS layer 406. The configuration of these slot antennas is described in further detail with respect to FIGS. 4A and 4B.

As shown in FIGS. 4A and 4B, the MS layer 406 is arranged to include a rectangular annular slot 416 and a nested circular annular slot 418, dividing MS layer 406 into three regions 406A, 406B, and 406C.

The first feed 410 is configured to operate in conjunction with the circular annular slot 418 to provide a circular annular slot antenna. Further, the first feed 410 is arranged in a coaxial manner. That is, the first feed includes an inner conductor portion 410A that connects to region 406C and an outer conductor portion 410B that is connected to region 406B. The second feed 412 is configured to operate in conjunction with the rectangular annular slot 416 to provide a rectangular annular slot antenna. Further, the second feed 412 is also arranged in a coaxial manner. That is, the second feed 412 includes an inner conductor portion 412A that connects to region 406B and an outer conductor portion 412B that is connected to region 406A. The outer conductor portions 410B and 412B can be formed via partial metallization of bottom of the substrate 402.

In operation, signals are directed via the second feed 412 to operate the rectangular annular antenna defined by the rectangular annular slot 416 to provide microwave heating of the tissue 414. Thereafter, a radiometer, coupled via first feed 410 to the circular annular antenna defined by circular annular slot 418 can be used to collect signals corresponding to the microwave radiation emitted by the tissue 414 as it cools down to track the temperature decay rate of the tissue 414.

System Implementation Considerations

Before the design is laboratory or clinically tested it should be made certain that several issues have been properly addressed:

LNA: LNA is a key component for achieving high radiometric sensitivity. In particular, low noise improves performance. Accordingly, to exploit the best noise figure performance from low noise transistors, the circuit can be fabricated on substrate with very low loss tangent. For example, aluminum oxide (alumina) can be used, which has a loss tangent in the order of 0.0002.

Packaging/Shielding: Because of the large gain required to amplify the thermal noise through the system, any feedback leakage created through radiation from printed circuit traces, imperfect grounding, improper RF shielding, and insufficient blocking of the RF path to supply voltage could generate random spurious oscillations. Therefore, careful design considerations should be incorporated to prevent such undesired effects. For example, most of the system gain can be assigned to the IF stage (0-170 MHz), at which spurious can be better suppressed. Furthermore, proper shielding of the unit by using microwave shielding/absorbing material can be provided to diminish external electromagnetic interference (EMI).

System Size: To reduce the system size, analog parts after the front stage (synthesizer, mixer, low pass filter, and IF stage) can be integrated in one module.

Frequency Channel Selection: Operation at different microwave frequency range provides flexibility in terms of the "depth of interrogation" with tissue and tuning to channels with minimum interferences. For example, interference from cell phones signals (850 and 1900 MHz bands) and Wi-Fi signals (2.4 GHz). Such FCC approved 0.9 and 2.4 GHz industrial-scientific-medical (ISM) bands should be examined for achieving the best compromise in terms of penetration depth and antenna size. 2.4 GHz heating may be of particular interest since the heating antenna will be significantly reduced (less than $L_x=L_y=2$ cm, compared to $L_x=L_y=4.2$ cm in FIG. 4A). Further, since the radiometer does not emit any signal, there is no regulatory restriction in terms of its frequency range, as long as emission from its RF components could be prevented by proper package design. However, a system in accordance with the various embodiments can be configured to operate in the range of 1-4 GHz (commonly used for medical radiometers) to provide flexibility in terms of penetration depth and tissue type. One difficulty could be the achievement of such wide frequency selectivity with one phase locked loop (PLL) synthesizer. In that case, one can use two synthesizers covering different portions of the range (1-2.5 GHz and 2.5-4 GHz) and switch between them as needed.

Antenna: As further discussed below, the radiometer antennas discussed herein primarily are directed to ranges of roughly 1-2 GHz. However, the various embodiments are not limited in this regard and the antenna bandwidth can be increased further, such as to 1-4 GHz or even wider. For example, additional nested slots can be provided or spiral-shaped antennas. Furthermore, the antenna can be implemented in flexible substrate such as Rogers Liquid Crystalline Polymer (LCP) ULTRALAM 3000 or a textile antenna. Such antennas can be conformed to the body shape.

Power Amplifier: Although the systems described herein were initially implemented using an off-the-shelf power amplifier (PA) for microwave heating, the various embodiments are not limited in this regard. For example, an alternate technique for efficient signal generation is using a class E Colpitts power oscillator topology discussed in Devine "Class E Colpitts Oscillator for Low Power Wireless Applications," *Electronics Letters*, Vol. 44, No. 21, pp. 1257-1258, October 2008. The drain efficiency (DE) of close to 50% at 900 MHz has been demonstrated for this technique. Further, other power sources can be used. For example, a compact and efficient solution for microwave heating can be to use a high power transistor such as NXP-BLF571 LDMOS (20 W rating). With 50% efficiency, 10 W RF signal can be generated from such a transistor using 12 V supply at 1.67 A current (20 W DC power). Further, advances in lithium-ion technology has led to compact rechargeable batteries with several Ah capacity (e.g., 12 V, 7 Ah), capable of supplying loads with over 1 A of current for over one hour. Therefore, integration of microwave heating source in a portable system can be achieved. Also, because of the lack of PA driver and high efficiency, the required heat sink and cooling system will be less bulky than general purpose PAs.

Perfusion Estimation

Different strategies can be employed to estimate the perfusion from measurements performed by this system. In one approach, a fixed power can be applied to the tissue, and the steady-state temperature elevation from the tissue background temperature can be recorded (step-response method). Alternatively, the steady-state temperature decay response can be also recorded by turning off the microwave heat source after the steady-state temperature elevation is reached. The perfusion then can be obtained by the temperature rise or decay waveform and its steady-state value. This can be done in a manner similar to the perfusion estimation from a convective perfusion probe technique used in Mudaliar et al, "A Phantom Tissue System for the Calibration of Perfusion Measurements," *J Biomech Eng.*, 130(5), October 2008, the contents of which are herein incorporated by reference in their entirety. In this technique, a heat flux gage is used to measure the heat flux response of tissue when convective cooling is applied. The measured and calculated heat flux data are used to determine perfusion by minimizing an objective function containing both measured and experimental data. The calculated data are obtained from a finite-difference model based on the well-known Pennes bioheat equation.

The calculation starts with an initial guess of the pertinent tissue parameters, which are iteratively updated until a desired convergence is reached. The algorithm for convective cooling method estimates both perfusion and thermal contact resistance. Microwave heating adds another aspect to such a parameter estimation method. Maxwell's equation need to be solved to find specific absorption rate (SAR) that will be applied as the source of heat generation in the Pennes equation (Equation (2)), modified by incorporating microwave heating (SAR).

$$\nabla \cdot (k \nabla T) - (\rho C w)_b (T - T_a) + \rho_t SAR + q_m = C_t \rho_t \frac{dT}{dt} \quad (2)$$

where $\rho_t$ and $\rho_b$ are mass density of tissue and blood, $C_t$ and $C_b$ are specific heat of tissue and blood, T is the tissue temperature, $T_a$ is arterial temperature (usually 37° C.), k is the thermal conductivity of tissue, $w_b$ is the blood perfusion rate, and SAR is the specific absorption rate (SAR=$\sigma E^2/2\rho_t$, E: electric field intensity, $\sigma$: electric conductivity) from the microwave absorption in tissue. $\rho_t SAR$ represents the volumetric heat generation due to microwave absorption and is larger than $q_m$ the metabolic heat generation. Solution of Equation 2 should be performed numerically for accurate evaluation of heat transfer. Nonetheless, a crude estimate of the solution can also be obtained. Assuming a one-dimensional problem of a region of length L, whose temperature is elevated by a certain value, the heating/cooling exponential decay/rise occurs with a time constant in the order of roughly $L^2/\pi^2 \alpha$, where $\alpha$ (=k/$\rho$C) is thermal diffusivity of the tissue. For L=2 cm, $\rho$=1060 kg/m$^3$, k=0.5 W/m·° C., and C=3600 J/kg·° C., this time constant is about 310 seconds. This is comparable to time constant associated for perfusion of about 330 seconds (1/w, w=0.003 mL/gr·s for skin). Therefore, the effect of cooling by perfusion is distinguishable from the conductive cooling for the heating region of 2 cm in length.

Equation (2) can be solved in a computing device, such as the controller of FIGS. 3A and 3B or an external computing device, using finite element or finite difference method, while the temperature information is streamed wirelessly to the computing device. Parameters in Equation (2), particularly $w_b$ and k are iteratively updated till a proper convergence of the objective function is achieved. SAR can be simultaneously modeled by solving Maxwell's equations using a computational electromagnetic model such as finite difference time domain or finite element method. Because, computational methods are very resource demanding, a more practical approach is to run Equation (2) in advance for various ranges of the parameters and obtain a dataset of "cooling" or "heating" curves or models. A similar process can be performed for SAR induced by the heating antenna in different tissue composition, to generate a SAR dataset. For instance, the user can input patient related data and the site of perfusion measurement (e.g. chest or back), and a closest SAR model would be looked up from the available library of dataset models that may best describe the SAR for the inputted specifications. Such preexisting library of SAR and temperature rise/cool dataset would remove the need for running resource hungry and slow computational algorithms in "real time". Such perfusion estimation algorithms could be run real-time in the processing unit inside the microwave perfusion device which would display the estimated perfusion. In an alternative method, the microwave device can stream data to simple mobile devices such as smartphones, where the application for perfusion estimation and display would reside and run.

Besides the step-response method, a repetitive sequence of ON and OFF state of the power amplifier (PA) can be employed (i.e. pulse method). Depending on the level of power applied, the rate of cooling due to perfusion and thermal conductivity, the duration of ON and OFF cycles, and random drift, the steady-state condition for high and low temperature baseline levels may or may not be reached at each cycle. If the steady-state is reached at each cycle, this is essentially similar to the step-response method, while parameter estimation can be performed on each cycle independently and the estimated parameters can be averaged for a better accuracy. On the other hand, if baselines for low and high change from each cycle to the next one, they could be regarded as non-stationary and slow processes of variation of baselines that could be removed by appropriate signal processing algorithms prior to parameter estimation.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the invention.

Preliminary Studies of the Radiometer System with if Module

Figure 5:
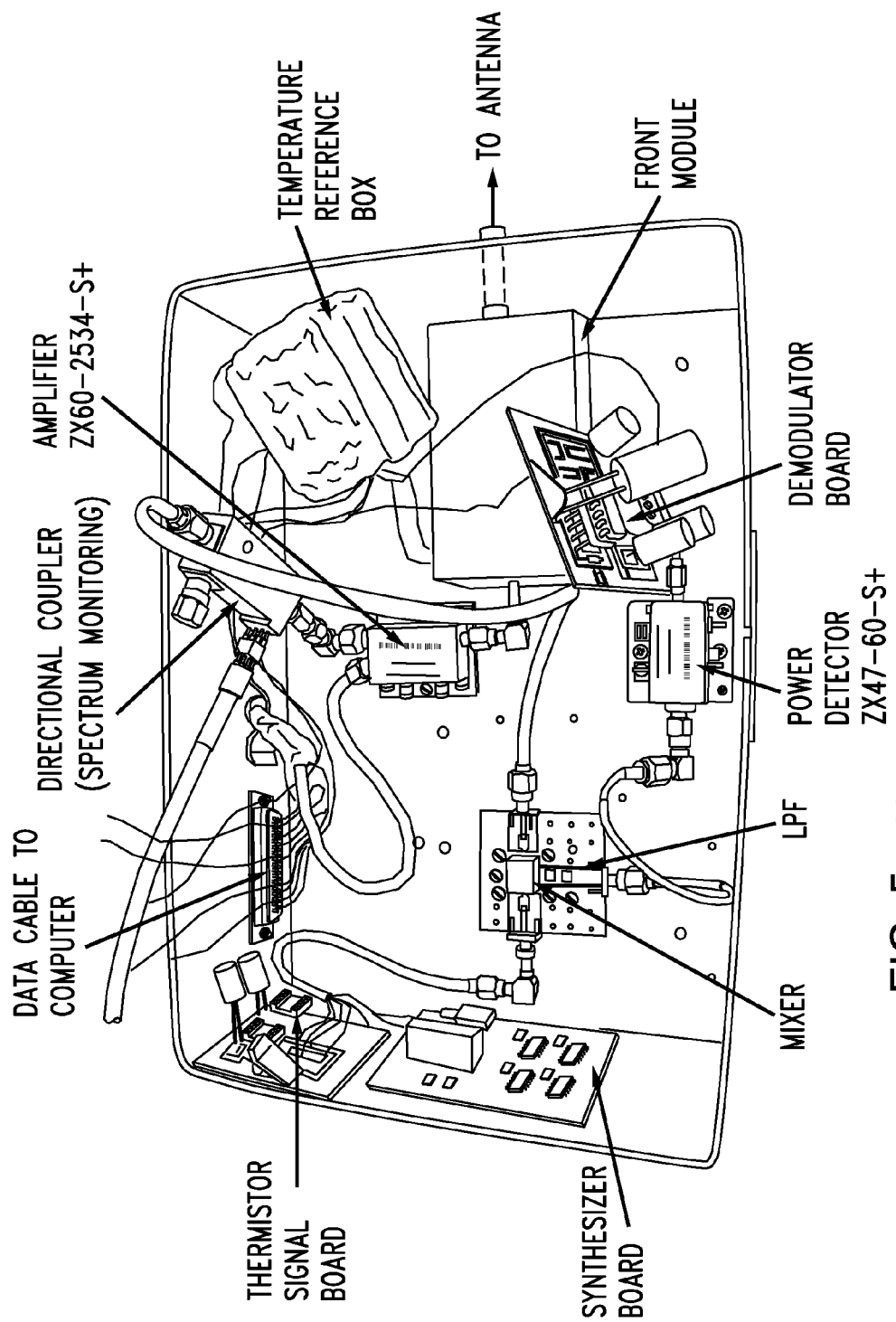
FIG. 5 shows a photo of an exemplary system in accordance with the various embodiments.

Two concentric annular slot antennas (applicators), configured as a dual-mode structure as described above with respect to FIG. 4A-4C, were chosen for a preliminary study. The circular slot is for radiometry at the 1-2 GHz range and the rectangular one for heating at the 900 MHz ISM frequency band. For improved matching and avoiding excessive specific absorption rate (SAR) in tissue, they are coated with a 2.5 mm-thick layer of silicone rubber. High frequency structure simulator (HFSS, ANSYS) simulation reveals a maximum SAR of about 60 W/kg per 1 W antenna input power occurring above the feed point in tissue. Maximum SAR would be three orders of magnitude higher without the coating. A preliminary system prototype is built and consists of SAV-541+ PHEMT LNA (MiniCircuits), switch (HMC270, Hittite), Amplifier2 (BGA 2716, NXP Semiconductors, plus ZX60-2534-S+, MiniCircuits), mixer (SYM-30DLHW, MiniCircuits), synthesizer (LMX2433, National Semiconductors), and Amplifier3/power detector (ZX47-60-S+, MiniCircuits). PC interfacing is through an NI DAQ board (PCI-6281). The configuration of these elements is illustrated by system 500 in FIG. 5.

Figure 6:
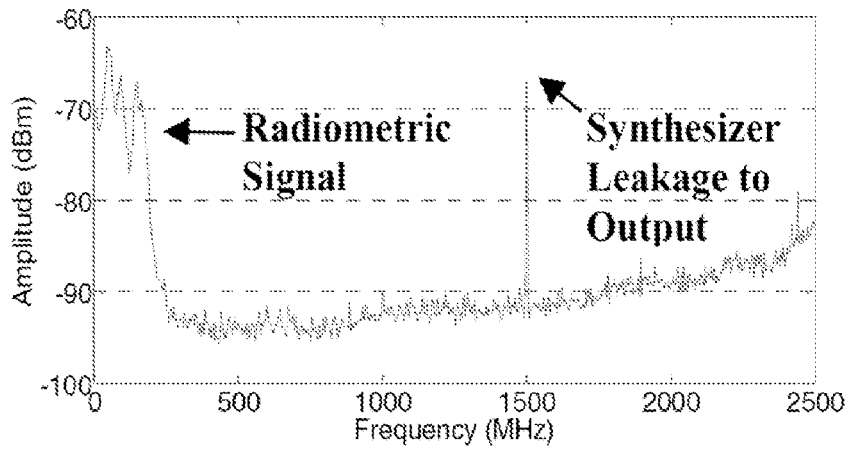
FIG. 6 is a plot showing a typical spectrum of amplitude as a function of frequency captured prior to the detector, with the synthesizer set at 1500 MHz and the switch in FIG. 3A is fixed at the antenna position.

The radiometric voltage read by the system was compared against a thermistor immersed 1 cm below the antenna facing tissue phantom liquid in a beaker, placed on a magnetic stirrer with hotplate, to uniformly raise the liquid's temperature. The phantom is composed of 58% distilled water, 41% sugar, and 1% salt, mimicking muscle permittivity. This is very similar to the Agar gel phantom described below, with the exception that the Agar is not used such that the phantom remains a liquid. Permittivity measurements performed by the inventor did not reveal significant differences in permittivity with and without 1% Agar material used as the gelling agent. FIG. 6 is a plot 600 showing a typical spectrum of amplitude as a function of frequency captured prior to the detector. In particular, FIG. 6 shows the output signal (before detector) with the synthesizer set at 1500 MHz, and the switch in FIG. 3A is fixed at the antenna position. Radiometric signal is seen at about 0-170 MHz, bandlimited by the LPF or BPF (custom-designed LC) in FIG. 3A or 3B.

Figure 7:
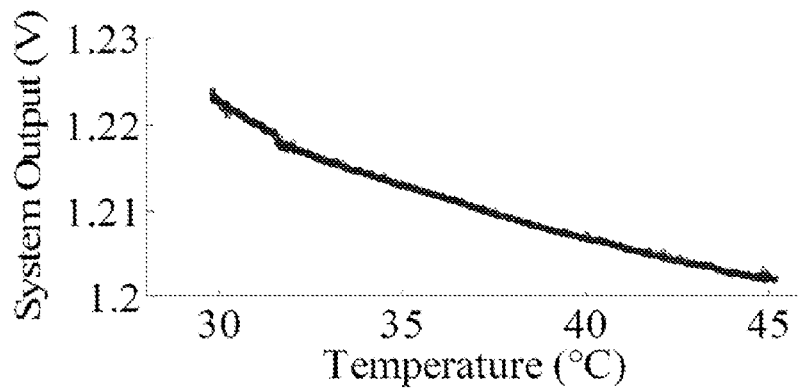
FIG. 7 is a plot of output voltage after the detector versus temperature with the synthesizer set at 1600 MHz and 2 seconds averaging, and the switch in FIG. 3A is fixed at the antenna position.

The detected output voltage versus temperature ("calibration curve") is illustrated in FIG. 7. FIG. 7 is a plot 700 of output voltage versus temperature with the synthesizer set at 1600 MHz and 2 seconds averaging. The graph shows a sensitivity of the system of 1.5 mV/° C. The main challenges faced have been spurious oscillations due to high system gain and interferences picked up by system components, mainly the reference temperature regulating circuitry. To avoid these adverse effects, currently, the switching can be disabled and attenuators can be added in the forward pass.

Figure 8:
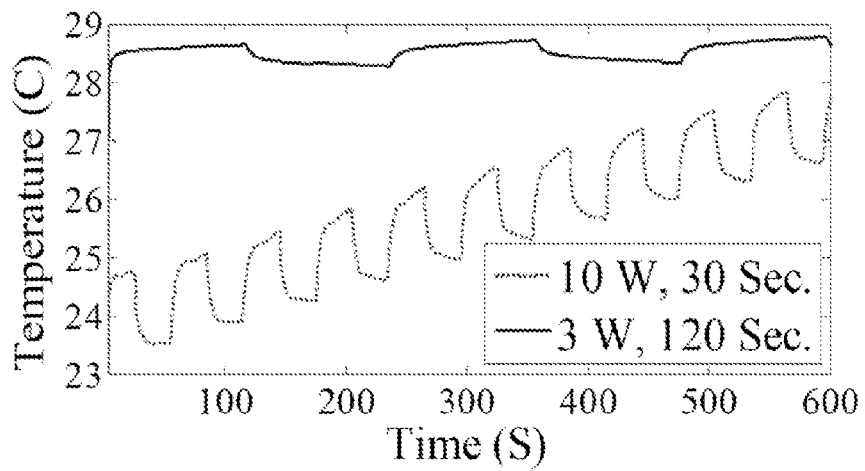
FIG. 8 shows a plot of temperature readings for 10 W on period for 30 seconds and 3 W on period for 120 seconds on-off PA cycles (the same on and off periods)

To understand the heating process, the power amplifier (PA, LZY-2+, Mini-Circuit, Brooklyn, N.Y.) is turned on and off, and the temperature is read by the thermistor (at about 1 cm depth). To avoid the possibility of damage to the radiometer's low power components, till proper protection is in place, the radiometer is disconnected and the related antenna port is replaced with a 50Ω load. FIG. 8 shows a plot 800 of temperature readings for 10 W on period for 30 seconds and 3 W on period for 120 seconds on-off PA cycles (the same on and off periods). Temperature rises of 1.5° C. and 0.4° C. are observed for the two cases respectively.

Such measured temperature values are very sensitive to the depth at which the thermistor is placed. On the other hand, radiometric measurement is likely to provide larger temperature fluctuations than measured by this thermistor, for similar range of applied microwave power, as depths of only few millimeters contribute disproportionally more to the radiometric temperature collected by the antenna. This preliminary study suggested a microwave power range of about 3-5 W at 1-2 minutes for 0.5-1° C. increase in the temperature at a depth of over 1 cm.

Characterization of an Exemplary Dual Mode Antenna

In a second set of experiments, the inventor tested the dual mode antenna design shown in FIG. 4A to evaluate its performance. For these experiments, a device consisting of dual mode antenna, as shown in FIG. 4A, was constructed using Rogers 4003 laminate ($\epsilon_r$=3.38, tan δ=0.0027) with height h=1.524 mm (60 mils) as the substrate 402. A silicone rubber ($\epsilon_r$=3.7, tan δ=0.003, Silicone II from GE) coating (thickness of d=2.5 mm) was used as the supersubtrate 404. The tissue 414 was simulated by covering the device with a semi-infinite tissue medium, noting the penetration depth in tissue in the order of cm.

The MS layer 406 for the device was formed to define an inner circular (1.5 GHz center frequency, radiometry) and an outer square (0.9 GHz, heating) annular slot. In particular, the dimensions for the MS layer were selected to be, with reference back to FIGS. 4A-4C: $d_x=d_y=52$ mm, $L_x=L_y=42$ mm, $W_s=2$ mm, $W_r=1$ mm, D=28 mm, $G_1=14.5$ mm, $G_2=12$ mm, $D_1=5$ mm. The feeds 410 and 412 were formed using a partial metallization of the bottom of the substrate layer 402 ($G_1 \times G_2$). For each of the feeds 410 and 412 in the device, the outer conductor portions 410B and 412B were utilized to provide grounding contacts. Inner conductor portions 410A and 412B were used to carry signals from and to the device, respectively.

A method of design based on the characteristic impedance of the slot was used, from which the approximate length of the slot for best impedance match could be identified. First, the characteristic impedance ($Z_0=R_0+jX_0$) and propagation constant ($\gamma=\alpha+j\beta$) were simulated using a finite element simulator. Note that the desired SAR profile would have even symmetry around the plane containing the feed (e.g., x-z plane for the circular annular slot in FIGS. 4A-4C). This implies the presence of a magnetic wall (open) at this plane. For an overall slot length of L, the input impedance at the feed point is then Z/2, where Z is the open terminated impedance of the line for length L/2:

$$Z=Z_0 coth(\gamma L/2) \quad (3)$$

Figure 9A:
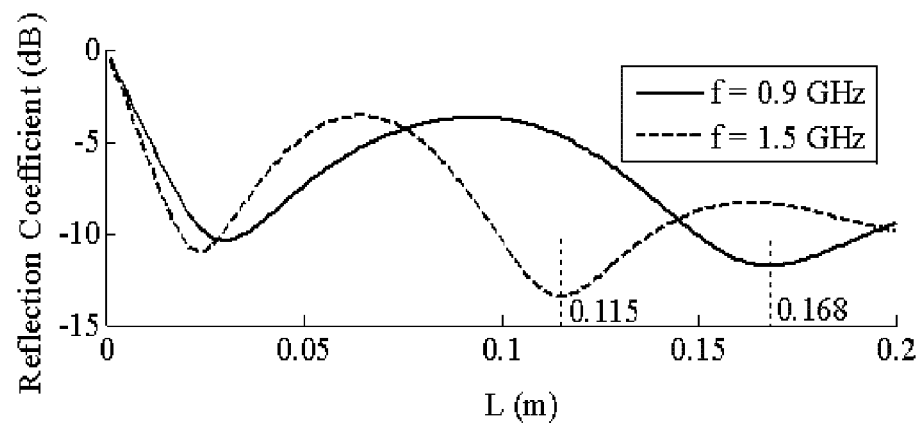
FIG. 9A shows a x-y plot of reflection coefficient versus slotline length at 1.5 and 0.9 GHz (w=1 mm)
Figure 9B:
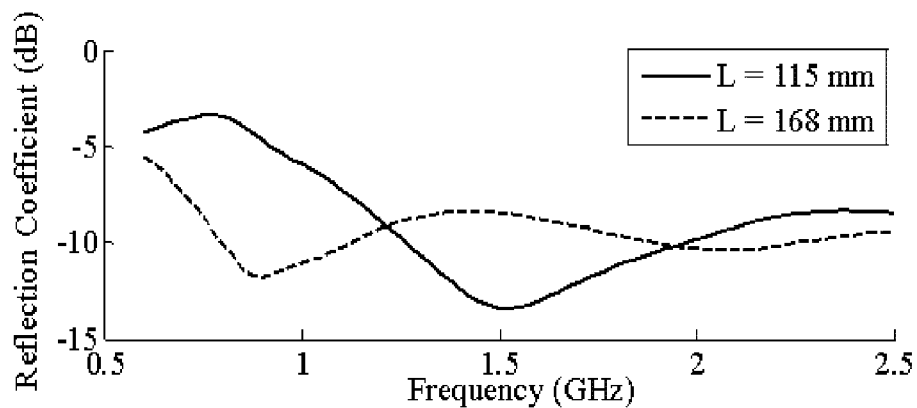
FIG. 9B shows a x-y plot of reflection coefficient versus frequency for L=115 mm and L=168 mm (w=1 mm)

The slot length L, for the maximum power transfer to the tissue, is then chosen when the input reflection coefficient (with respect to 50Ω) is at its minimum (slotline width w=1 mm) for muscle tissue, where L=115 mm and L=168 mm exhibit the lowest reflection coefficient at 1.5 and 0.9 GHz respectively. The slotline reflection coefficient versus frequency for these two lengths is shown in FIGS. 9A and 9B, also showing the lowest reflection coefficient at 1.5 and 0.9 GHz. FIG. 9A shows an x-y plot 900 of reflection coefficient versus slotline length at 1.5 and 0.9 GHz (w=1 mm). FIG. 9B shows a x-y plot 950 of reflection coefficient versus frequency for L=115 mm and L=168 mm (w=1 mm).

The above analysis implies the square annular slot with a side length of 42 mm (168 mm/4) for 0.9 GHz (heating) and the circular one with a diameter of 36.6 mm (115 mm/R) for L band radiometry (1 to 2 GHz). HFSS simulation of individual annular slot applicators verifies similar resonance frequencies to FIG. 9B. The annular slots are directly fed by coaxial lines instead of microstrip lines, as used elsewhere. After combining the two in a dual-mode configuration and introducing partial metallization in the backplane for coaxial feed attachment, further adjustment is necessary for maintaining low reflection coefficient at the desired frequencies, namely reduction in the diameter of the circular annular slot and increase in the width of the square one. Final dimensions are detailed above.

A simple feeding strategy is incorporated to keep the coupling between the two feeds ($S_{21}$) in FIG. 4A low, where the two feed points are spatially apart for 90° with respect to one another. Silicone superstrate assists in better uniformity of the SAR over the surface of the annular slot. The value of d=2.5 mm is selected as a compromise between having a smaller size heating applicator with low reflection coefficient at 0.9 GHz, and avoiding high SAR around the slot and its feed point, observed for thinner d. For silicone coating, a square opening of 45×45 $mm^2$ was cut from a 2.5 mm thick sheet (screen). The screen was then placed on the substrate. The silicone was deposited manually, and using a blade, its thickness was adjusted to that of the screen by gently removing the extra amount of silicone. After curing for 24 hours, the screen was removed. Then, additional amount of silicone was added to the uncoated area around the board's edge, was tapered down to the edge, and was left for further curing.

An Agar based phantom was prepared for the measurement. It was chosen because it is non-toxic and can be prepared by readily available ingredients. The muscle phantom consisted of a mixture of (by weight) 57% distilled water, 41% sugar, 1% NaCl, and 1% Agar powder. The mixture was poured in a cubic shape glass container (9.5×9.5 $cm^2$ cross section, 8 cm height) and heated to about 85° C. in a microwave oven. The mixture was then stirred and left to cool to the room temperature to form the gel.

The gel complex permittivity was measured at room temperature (23° C.) by a 3.5 mm coaxial probe. The probe was made from a 6-inch-long semi-flexible cable with its open end carefully ground down. The measured phantom dielectric parameters were $\epsilon_r$=55.8 and σ=1.10 S/m at 0.9 GHz, and $\epsilon_r$=52.0 and σ=1.64 S/m at 1.5 GHz. The reference liquids used were distilled water, methanol, and saline (N=1).

Figure 10A:
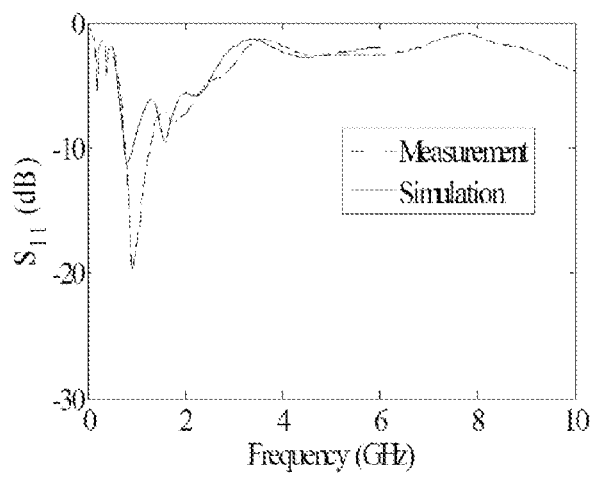
FIGS. 10A, 10B, and 10C are x-y plots of measured and simulated $S_{11}$, $S_{22}$, and $S_{21}$, respectively, for the two antennas of FIGS. 4A-4C, where ports 1 and 2 are the square and circular annular slots, respectively.
Figure 10B:
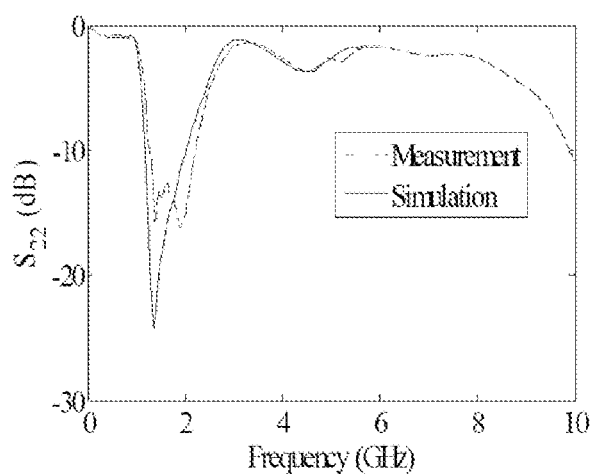
Figure 10C:
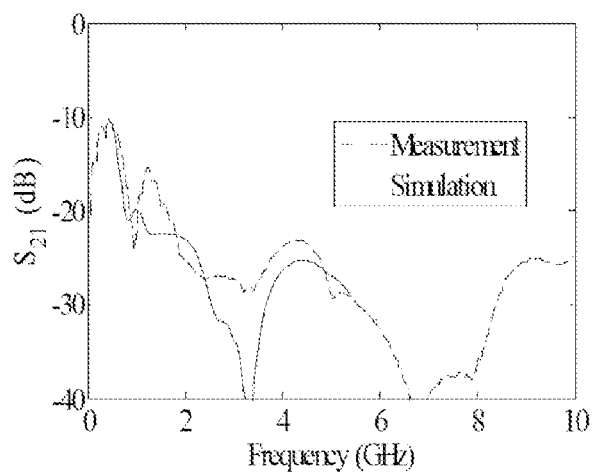

HP 8720C vector network analyzer (VNA) was used for cables and was used for measuring the applicator's S parameters, as well as the permittivity as mentioned above. FIGS. 10A, 10B, and 10C show plots 1000, 1025, and 1050 illustrating $S_{11}$, $S_{22}$, and $S_{21}$, respectively, for the two antennas of FIG. 4A, where ports 1 and 2 are the square and circular annular slots respectively. The antenna is placed against a muscle phantom, i.e., Agar gel. A summary of the dual-mode performance at frequencies of interest is listed at Table I. Measurements compare well against the simulation results at frequencies of interest, i.e., where return loss ($S_{11}$ and $S_{22}$) of −10 dB or better and $S_{21}$ of about −20 dB (at the heating frequency of 0.9 GHz) or better may be desirable.

TABLE I

SUMMARY OF DUAL-MODE ANTENNA'S PERFORMANCE
AT THE FREQUENCIES OF INTEREST

|  | $S_{11}$ at 0.9 GHz (dB) | $S_{21}$ at 0.9 GHz (dB) | $S_{22}$ at 1.5 GHz (dB) | $S_{22}$ at 2 GHz (dB) | $S_{22}$ 10-dB BW (GHz) |
|---|---|---|---|---|---|
| Simulation | −10.3 | −20.6 | −18.8 | −10.3 | 0.84 |
| Measurement | −18.7 | −21.1 | −13.7 | −15.1 | 0.95 |

Because of the texture of the phantom, which is soft and moist, the measured S parameters are not completely identical for repeated measurement runs. The results shown in FIGS. 10A-10C and Table I are from a sample run. They may vary, particularly around the notches in FIGS. 10A-10C, with the amount of pressure exerted to maintain the applicator against the gel. Nonetheless, the results compare well to the simulation results at frequencies of interest. In general, a return loss ($S_{11}$ and $S_{22}$) of about −10 dB or better, and a $S_{21}$ of about −20 dB (at the heating frequency of 0.9 GHz) or better are desirable.

Figure 11A:
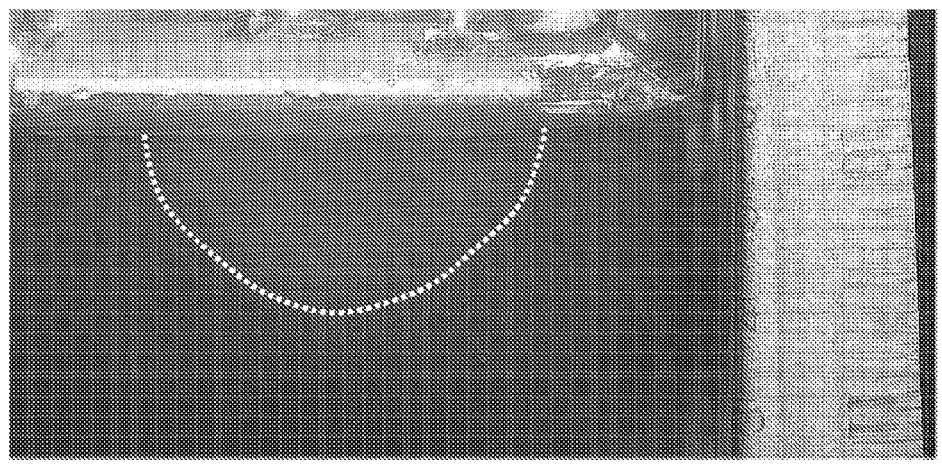
FIGS. 11A and 11B show the heating profile registered on temperature sensitive film for the y-z and x-z cross sectional planes, respectively, of an Agar gel in response to heating using the dual mode antenna of FIGS. 4A-4C.
Figure 11B:
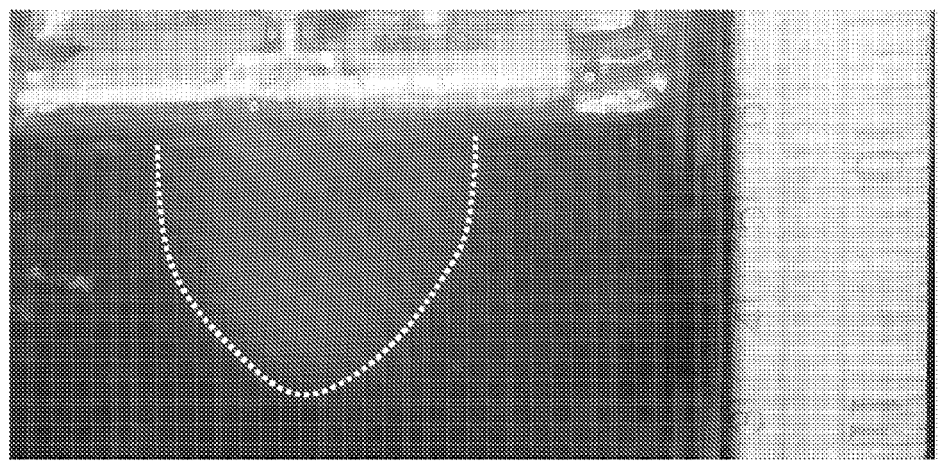

To observe the heating profile, a temperature sensitive liquid crystal sheet (25-30° C., Edmund Scientific) was inserted inside the phantom mixture before the gel is formed. Port 2 was matched, and 14 W of power was applied to port 1, for a duration of 70 seconds (room and initial gel temperature of 23° C.), through a setup consisting of a signal generator (Anritsu MG3691B) and a power amplifier (Minicircuits LZY-2). FIGS. 11A and 11B show photos 1100 and 1150, respectively, of the heating profile registered on the temperature sensitive film for the y-z and x-z cross sectional planes, respectively. Note that although the Agar gel is not completely transparent, the region with temperature rise of 2° C. or more is clearly registered by the sheet and extended to a depth of about 2-2.5 cm (0.75"-1"). The deeper penetration appeared for the x-z cross section is due to the fact that the gel may have not completely reached the room temperature between the two measurements. A wider heating profile on the feed plane (y-z plane) compared to the one for the x-z plane is observed and agrees with the literature for similar slot lengths.

Compared with the dual-mode designs described elsewhere, where a microstrip network feeds a patch on the backplane, and a spiral antenna is used for radiometry, the metallization and feed for the structure in FIGS. 4A-4C is less complex overall. Lowering the feed line loss by using a short coaxial cable length as opposed to longer microstrip lines can be advantageous, bearing in mind that minimal degradation of the input noise temperature by the feed line is desirable for radiometric sensing. Although the annular slot's resonance length is usually obtained empirically through simulation, a method for the annular length design, based on the characteristics of the equivalent slotline was also presented here, as pertained to Equation (3) and FIG. 9A and FIG. 9B.

FIGS. 10A-10C and Table I suggest desirable return loss at the frequencies of interest and isolation ($S_{21}$) at the heating frequency of 0.9 GHz. The measured $S_{22}$ is better than −10 dB for a range of 1.26 to 2.21 GHz. This suggests a useful range for radiometry and the possibility of multifrequency operation, where few channels with approximately 200-300 MHz bandwidth can be utilized. This is consistent with FIG. 6, where a low pass bandwidth of 170 MHz corresponds to a band pass bandwidth of 340 MHz (2×170). For microwave hyperthermia treatment, a temperature rise of about 5° C. (more for ablation), corresponding to a typical applicator power of few tens of Watts or more is required. On the other hand, for blood perfusion evaluation a temperature rise of only up to 0.5-1° C. would be sufficient, implying a power of only a few Watts (e.g. less than 5 W). During the heating, the radiometer's front section can be turned off. Nonetheless, the power leakage to the radiometer (from the heating port), which is about 20 dB lower (Table I) should be within the tolerable range of the radiometer's input circuitry.

Radiometer System Characterization with No if Module

Figure 12:
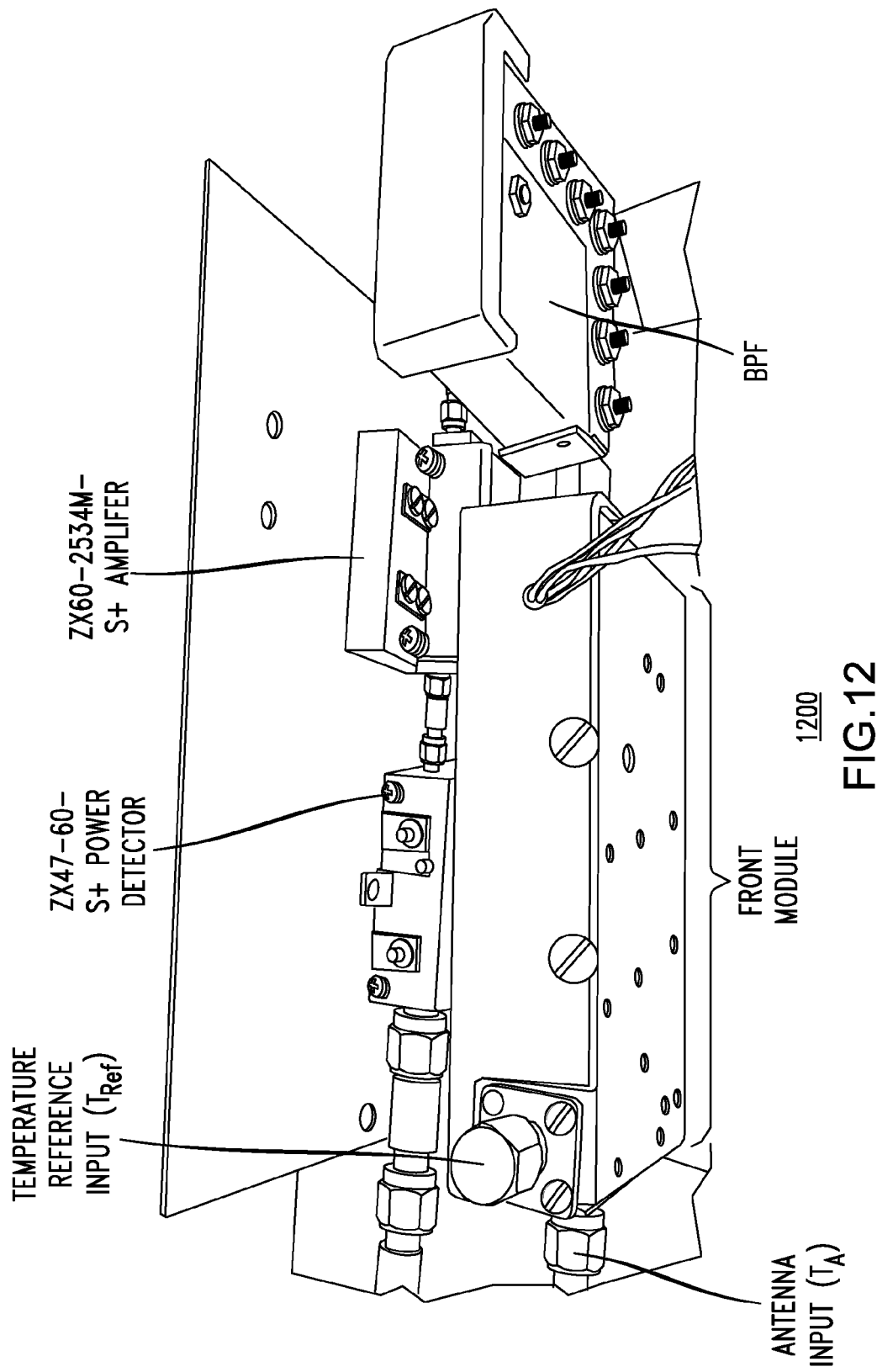
FIG. 12 is a photograph illustrating a radiometer in accordance with the various embodiments.

In addition to testing of the antenna design of FIG. 4A, a device implementing a radiometer with an operating frequency range of 1 to 2 GHz (L band) with a bandwidth of 300 MHz was also tested and characterized. The device was configured in a single channel mode, as described above. That is, the device does not include an intermediate frequency (IF) stage. The radiometer in the device was tuned to 1.5 GHz center frequency. The radiometer in the device also includes a dual-mode antenna, as described above, for L band radiometry and heating at 900 MHz ISM band. A bandpass filter (BPF) for a fixed radiometry range of 1.4-1.7 GHz was also used. FIG. 12 shows a device 1200 implementing the radiometer. The detector output of the device in FIG. 12 and other signals are interfaced to a PC, through a National Instruments DAQ board, PCI-6281 with 16 analog inputs, 24 digital input/output, 2 analog outputs, and SCB-68 Shielded I/O Connector Block for DAQ devices with 68-Pin connectors. This system comes with a SHC68-68-EPM shielded cable which connects the DAQ and the connector block. The rest of the process and display runs on the LabView software.

Circuit components for fabricating the exemplary device in FIG. 12 were obtained from Mini-Circuits Inc. (www.minicircuits.com, Brooklyn, N.Y.), Hittite Microwave Corporation (www.hittite.com, Chelmsford, Mass.), and NXP Semiconductors (www.nxp.com, Eindhoven, The Netherlands). Printed circuit board (PCB) for circuits and antennas can be fabricated on microwave substrates provided by Rogers Corporation (www.rogerscorp.com, Rogers, Conn.). Front module PCB and antenna were fabricated using a PCB milling machine from LPKF Lasers & Electronics (www.lpkfusa.com, Tualatin, Oreg.).

Figure 13A:
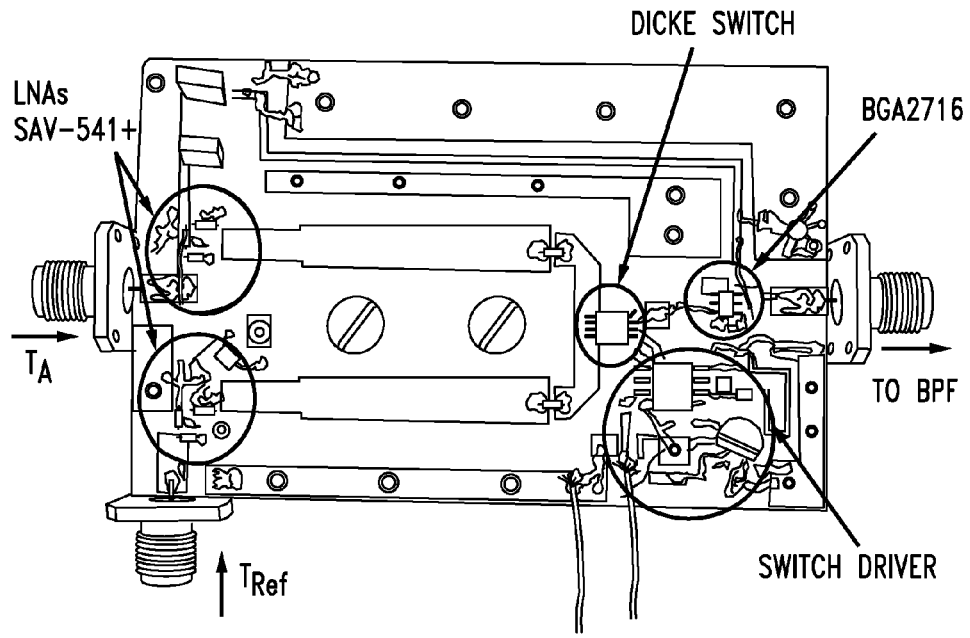
FIGS. 13A and 13B are photographs of alternate designs for a front module in accordance with the various embodiments.

The front module includes the two LNAs, a switch, and an amplifier after the switch, realized as one unit, similar to the configuration described above with respect to FIG. 3. Two different LNA designs for front module were tested. A first design utilized custom-designed LNAs featuring low noise PHEMT transistors (SAV-541+, Minicircuits, Brooklyn, N.Y.). This design for the front module is shown by front module 1300 in FIG. 13A. A second design, based on off-the-shelf LNA chips (MGA62563, Avago Technologies, San Jose, Calif.), is shown by front module 1350 in FIG. 13B.

Figure 13B:
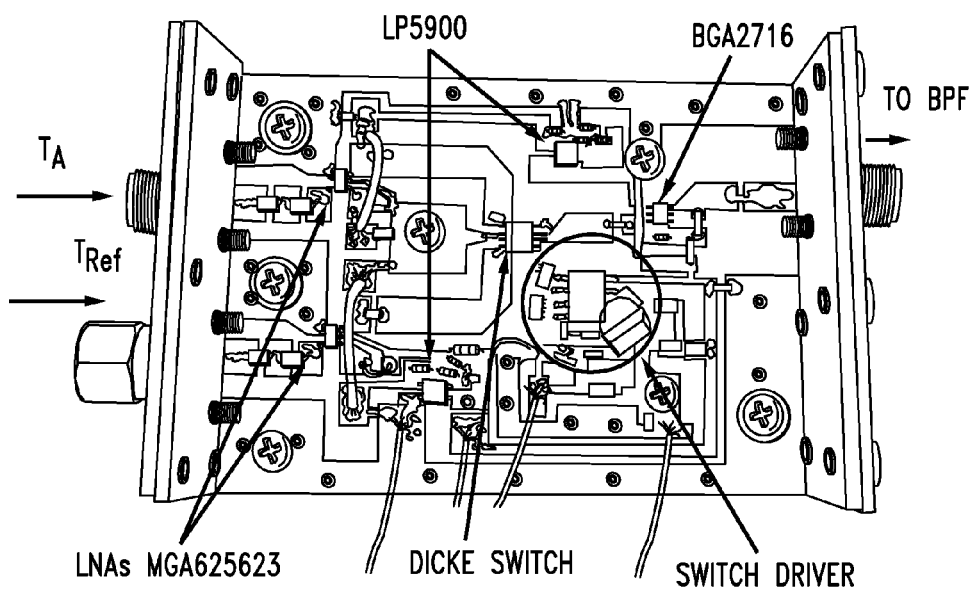

In either design, amplified input from the antenna ($T_A$) or a reference temperature regulated box ($T_{Ref}$) then passes through the Dicke switch (HMC270MS8G, Hittite, Chelmsford, Mass.), followed by a second amplification stage (BGA- 2716, NXP Semiconductors, San Jose, Calif. The first design, the SAV-541+ version for FIG. 13A, has lower noise figure but requires further packaging and grounding considerations to prevent undesired spurious oscillations, whereas the second design, the MGA62563 version of FIG. 13B, is easier to implement. Both versions work with ±5 V supply.

The Dicke switch is derived by a pair of operational amplifiers for generating 0 and −5 V switching signals from standard 0 and 5 V TTL. The MGA62563 version also includes 3 V voltage regulators (LP5900, Texas Instruments), to provide supply to the LNAs. The output from front module is fed to band pass filter of the rear module. This is followed by feeding the output to an amplifier (ZX60-2534M-S+, Minicircuits, Brooklyn, N.Y.) and a power detector (ZX47-60-S+, Minicircuits, Brooklyn, N.Y.).

Figure 14A:
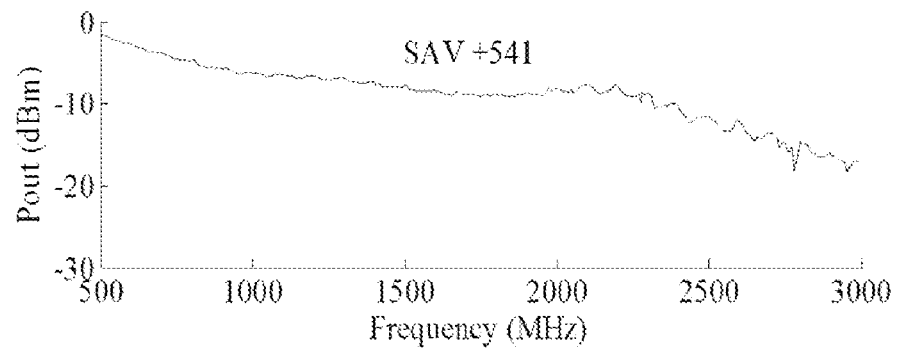
FIGS. 14A and 14B are x-y plots for output power (Pout) as a function of frequency for the designs of FIGS. 13A and 13B, respectively.
Figure 14B:
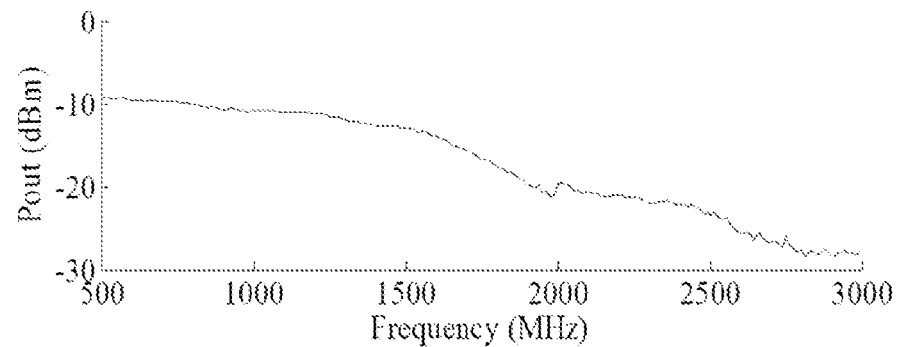

FIGS. 14A and 14B show x-y plots 1400 and 1450 of gain (Pout) as a function frequency for the front modules 1300 and 1350, respectively. The data in these plots was generated based on an input power of −50 dBm applied through an RF signal generator followed by an attenuator. Frequency was swept, and the output power obtained by a spectrum analyzer was recorded. As shown in FIGS. 14A and 14B, the designs demonstrate a gain of 42 dB for the SAV-541+ version and 37 dB for the MGA62563 version at 1.5 GHz.

Figure 15:
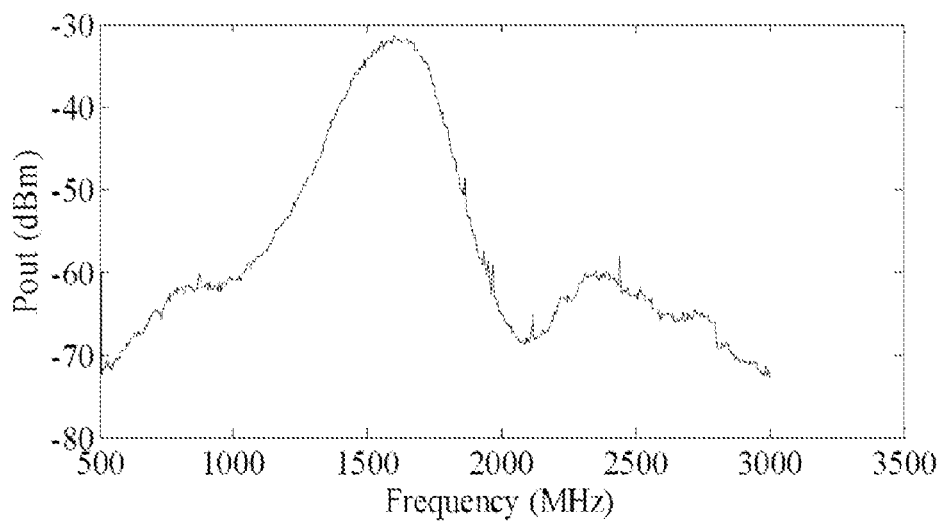
FIG. 15 is an x-y plot of the output power (Pout) spectrum prior to the power detector as a function of frequency for the design of FIG. 13A with both inputs terminated to 50Ω to show the output noise at room temperature.

With both inputs terminated to 50Ω (at room temperature), the output noise taken at the output of the ZX60-2534M-S+ amplifier (for the system with the SAV-541+ version and the antenna input selected by the switch) is shown in FIG. 15. FIG. 15 is an x-y plot of the output power (Pout) spectrum prior to the power detector as a function of frequency for the design of FIG. 13A with both inputs terminated to 50Ω to show the output noise at room temperature. A spectrum analyzer resolution bandwidth (RBW) of 1 MHz was selected. At room temperature, the input noise power density is kT (k: Boltzmann constant, T: temperature in ° K) or about −174 dBm/Hz. With 42 dB gain from Unit 1, 6 dB insertion loss from the BPF, 39 dB gain from the ZX60-2534M-S+ amplifier, and 300 MHz (85 dB·Hz) system bandwidth, the ZX60-2534M-S+ output signal (for a noise free system) is estimated to be about −14 dBm (−39 dBm/MHz) at around 1.5 GHz. However, this calculated spectrum is lower than what is measured in FIGS. 14A and 14B, because of the added internal noise due to the system circuitry and the spectrum analyzer.

Perfusion Estimation Tests

To investigate the effect of heat/cool variation upon PA ON-OFF sequence, the setup of FIG. 15 was implemented. The dual-mode antenna of FIG. 4 is used for this setup as the antenna 1602. Water is circulated by a temperature regulated bath/pump system 1604 (RTE-8DD, Neslab Endocal) through a Plexiglas container 1606 which is tapered at the two sides for generating uniform flow under the antenna 1602. The flow rate is controllable by valves available in the bath/pump system 1604 and a flowmeter 1608 (Dwyer Instruments) used for measuring the amount of flow. The antenna 1602 is held against the top wall of the container 1606 which is about 2-mm thick and has a dielectric constant close to silicone. Therefore, the antenna 1602 is coated with only a thin layer (less than 1 mm) silicone superstrate coating such that the overall dielectric thickness over the annular slots, including the Plexiglas wall, is comparable with what was used in previous studies (FIGS. 9A-9B and 10A-10C). For this heating/cooling experiment, the power amplifier (MS/PA) 1610 for a microwave source 1611 was connected to the square annular slot input of the antenna 1602, while the circular annular slot input of the antenna 1602 was terminated to a 50Ω coaxial termination. The temperature was measured by a thermistor 1612 placed about 1 cm below the antenna 1602. A circulator 1614 and a dummy load 1616 are also used to protect the power amplifier 1610 from large reflection from the antenna 1602 due to large mismatch occurring if the contact of the antenna 1602 with the tissue phantom medium (water in this case) was momentarily lost. A coupler 1618 was also used for monitoring the power at the antenna 1602 via a spectrum analyzer 1620.

Figure 17A:
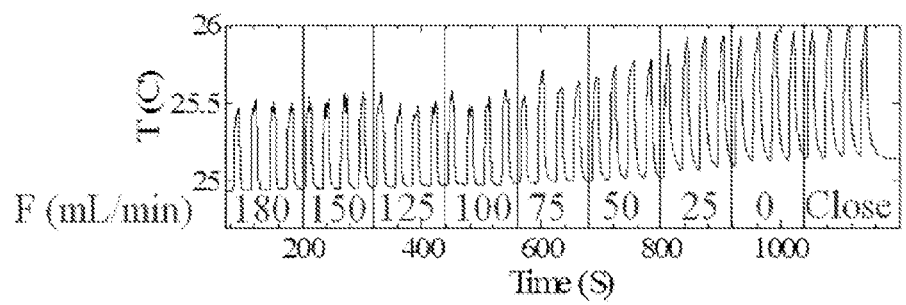
FIG. 17A is a plot of temperature as a function of time, as the flow rate was varied through the test device of FIG. 16.

FIG. 17A is a plot 1700 of temperature as a function of time, as the flow rate was varied. In particular, FIG. 17A illustrates the temperature variation, while the flow is kept constant for 4 full cycles. The measurement parameters are PA power of P=1 W, on time=10 s, off time=20 s, regulated bath temperature $T_{Reg}$=24.7° C. An averaging window of 0.3 s is applied to the temperature data. The thermistor is placed at a depth of about 1 cm.

Figure 17B:
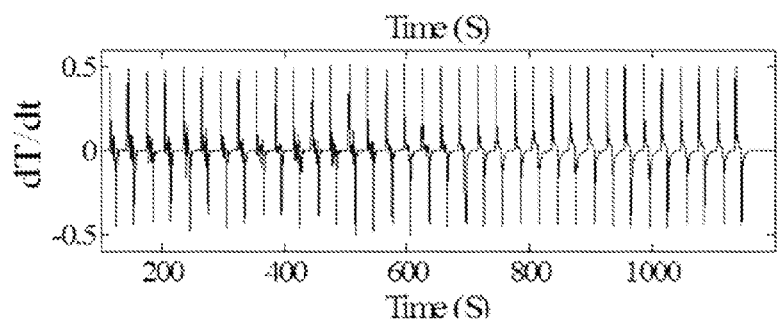
FIG. 17B is a plot of the derivative of the temperature with time for the data in FIG. 17A.

FIG. 17B is a plot 1750 of the derivative of the temperature with time for the data in FIG. 17A. It may be first speculated that if such temperature rise and decay are exponentially varying, the slope (i.e. derivative) at the instances of pulse becoming ON or OFF would correspond to a time constant that may vary with the flow rate. However, FIG. 17B clearly indicates that this quantity is almost independent of the flow (i.e. the observed peaks at the instances of pulse becoming ON or OFF). On the other hand, it is known that for short time durations SAR=CdT/dt (C is the specific heat). Therefore, spikes in FIG. 17B that are almost independent of the flow rate can be exploited to estimate SAR quite easily, while perfusion (w) and thermal conductivity (k) may require a parameter estimation algorithm as discussed previously to be estimated.

Figure 18:
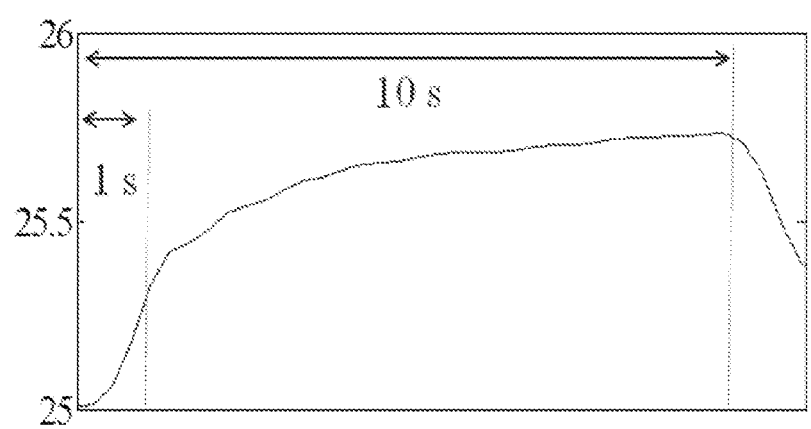
FIG. 18 is plot showing a magnified view of one heat cycle in FIG. 17A.

FIG. 18 is a plot 1800 showing a magnified view of one heat cycle in FIG. 17A, where the initial rise could be exploited for SAR measurement, and the follow up "exponential-like" trajectory could be exploited to estimate w, as well as other parameters such as k, through a parameter estimation algorithm. Such parameters can be equally obtained from the cool cycle which has a similar initial SAR related fall followed by an exponential-like decay for the rest of the period.

SAR generated by the heating antennas is influenced by the antenna/skin contact, in such a way that the antenna's power reflection coefficient (known as $|\Gamma|^2$) may be impacted by repositioning of the antenna on the skin. Knowing the PA power, the SAR estimation method described above can be used to calibrate for such random changes of the antenna reflection coefficient. Also note that when the temperature is read by the radiometer, the radiometric temperature T and the estimated SAR would be average values of their spatial profiles which would be weighted by the receiving antenna's near-field power beam W(x,y,z). In other words, the radiometric temperature would be the well-known relation:

$$T = \frac{\iiint W(x, y, z)T(x, y, z)dxdydz}{\iiint W(x, y, z)dxdydz} \tag{4}$$

Figure 16:
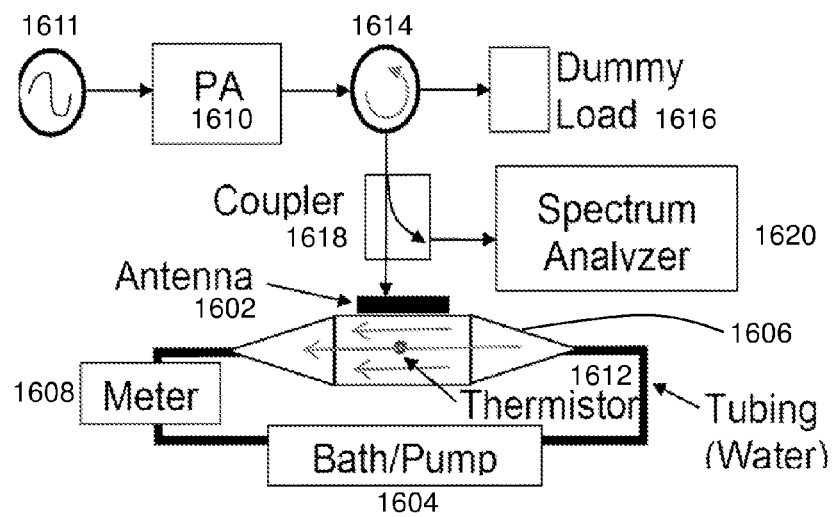
FIG. 16 is a setup for investigation of heat/cool signatures during PA on-off sequence, where the microwave power at 900 MHz is applied through the heating input of the antenna in FIG. 4 to a water phantom flowing in a Plexiglas container at variable rates controllable by a temperature regulated bath/pump system and a flowmeter.

Finally, it should be mentioned that perfusion cannot be accurately mimicked by the setup of FIG. 16, where water is flowing freely and the movement is directional. For mimicking perfusion, setups using a porous phantom, such as water flowing through a sponge, can be implemented as described elsewhere by Mudaliar et al, "A Phantom Tissue System for the Calibration of Perfusion Measurements," *J Biomech Eng.*, 130(5), October 2008, the contents of which are herein incorporated by reference in their entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A system, comprising:
    a dual mode antenna defining a first slot antenna and a second slot antenna;
    a microwave radiometer coupled to the first slot antenna;
    a microwave source coupled to the second slot antenna; and
    a controller coupled to the microwave radiometer and the microwave source,
    wherein the controller operates the dual mode antenna in a heating mode via operation of the microwave source and in a temperature measurement mode via operation of the microwave radiometer, and
    wherein the dual mode antenna comprises:
        a metallization layer having a first annular slot defining the first slot antenna and a second annular slot defining the second slot antenna, wherein the first annular slot is nested with respect to the second annular slot;
        a first feed comprising a coaxial feed configured for directing a signal from a first region of the metallization layer inside the first annular slot to the microwave radiometer and providing a reference signal to a second region of the metallization layer between the first annular slot and the second annular slot, and
        a second feed comprising a coaxial feed configured for providing a signal from the microwave source to the second region and providing a reference signal to a third region of the metallization layer outside the second annular slot.

2. The system of claim 1, wherein the dual mode antenna further comprises a substrate layer supporting the metallization layer, a superstrate layer disposed on the metallization layer.

3. The system of claim 1, wherein the first annular slot extends along a circular path and wherein the second annular slot extends along a rectangular path.

4. The system of claim 1, wherein the first and the second feeds are disposed at positions separated by approximately 90 degrees with respect to the nested structure.

5. The system of claim 1, wherein the microwave radiometer comprises a front module coupled to the first slot antenna and a rear module coupling the front module to the controller, the front module comprising:
    a two-way switch with an output port, a first input port, and a second input port,
    a first low noise amplifier (LNA) coupled between the first input port and the first slot antenna; and
    a second LNA coupled between the second input port and a reference load maintained at a constant temperature, wherein the first LNA and the second LNA are substantially identical, and wherein the two-way switch is controlled by the controller to selectively couple the output port to one of the first input port and the second input port.

6. The system of claim 5, wherein the microwave radiometer further comprises an intermediate frequency (IF) module coupling the front module to the rear module, the IF module comprising:
    a synthesizer; and
    a mixer;
    wherein the mixer receives an output of the front module, combines the output of the front module with an output of the synthesizer to yield a frequency down-converted output, and forwards the down-converted output to the rear module.

7. The system of claim 5, wherein the rear module comprises:
    a band pass filter having an input coupled to the front module or a low pass filter if an IF module is used; and
    a detector coupled having an input coupled to the output of the band pass filter and an output coupled to the controller.

8. The system of claim 1, wherein the controller processes output signals from the microwave radiometer to characterize a temperature of a biological tissue as a function of time to yield temperature characteristics and characterizes a biological function of the biological tissue based on the temperature characteristics.

9. A method, comprising:
    directing, during a first time period, microwave energy into a biological tissue using a first slot antenna defined by a first annular slot formed in a metallization layer;
    detecting, during a second time period subsequent to the first time period, microwave radiation emitted by the biological tissue using a second slot antenna defined by a second annular slot formed in the metallization layer and that is nested with respect to the first annular slot;
    generating output signals corresponding to the microwave radiation;
    processing the output signals to characterize a temperature of the biological tissue as a function of time to yield temperature characteristics; and
    characterizing a biological function of the biological tissue based on the temperature characteristics,
    wherein the directing comprises providing, via a first feed comprising a coaxial feed, signals from a microwave source to a first region of the metallization layer between the first annular slot and the second annular slot and a reference signal of the microwave source to a second region of the metallization layer outside the first annular slot, and wherein the detecting comprises directing, via a second feed comprising a coaxial feed, signals from a third region of the metallization layer inside the second annular slot to a microwave radiometer and providing, via the second feed, a reference signal of the microwave radiometer to the first region.

10. The method of claim 9, wherein the biological function is a blood perfusion rate.

11. The method of claim 9, further comprising selecting the first annular slot to extend along a rectangular path and the second annular slot to extend along a circular path.

12. The method of claim 9, wherein the generating comprises alternatively directing the signals from the third region through a first low noise amplifier (LNA) and a reference load a second LNA coupled to yield the output signals, wherein the first LNA and the second LNA are substantially identical.

13. The method of claim 9, wherein generating further comprises mixing the output signals with signals from a synthesizer to yield frequency down-converted output signals.

* * * * *